US007432077B1

(12) United States Patent
Haga et al.

(10) Patent No.: US 7,432,077 B1
(45) Date of Patent: Oct. 7, 2008

(54) HIGH-AFFINITY CHOLINE TRANSPORTER

(75) Inventors: Tatsuya Haga, Zushi (JP); Takashi Okuda, Hoya (JP)

(73) Assignee: Japan Science and Technology Agency, Kawaguchi-Shi, Saitama (JP)

( * ) Notice: Subject to any disclaimer, the term of this patent is extended or adjusted under 35 U.S.C. 154(b) by 320 days.

(21) Appl. No.: 10/069,541

(22) PCT Filed: Aug. 18, 2000

(86) PCT No.: PCT/JP00/05545

§ 371 (c)(1),
(2), (4) Date: Feb. 27, 2002

(87) PCT Pub. No.: WO01/16315

PCT Pub. Date: Mar. 8, 2001

(30) Foreign Application Priority Data

Aug. 27, 1999  (JP)  ................................ 11/240642
Dec. 27, 1999  (JP)  ................................ 11/368991

(51) Int. Cl.
*C12P 21/06* (2006.01)
*C12P 21/04* (2006.01)
*C12N 1/20* (2006.01)
*C07K 1/00* (2006.01)
*C07H 21/02* (2006.01)
*C07H 21/04* (2006.01)
*A61K 39/00* (2006.01)

(52) U.S. Cl. .................. 435/69.1; 435/69.7; 435/252.3; 424/185.1; 424/192.1; 530/350; 536/23.1; 536/23.4

(58) Field of Classification Search ................ 536/23.1, 536/23.4, 23.5; 435/325, 69.1; 530/300, 530/350
See application file for complete search history.

(56) References Cited

U.S. PATENT DOCUMENTS

| 4,946,778 | A | 8/1990 | Ladner et al. |
| 6,287,820 | B1 * | 9/2001 | Umansky et al. ............ 435/91.1 |
| 6,500,643 | B1 * | 12/2002 | Wu et al. .................... 435/69.1 |
| 2003/0022195 | A1 * | 1/2003 | Curits ............................ 435/6 |
| 2003/0114399 | A1 * | 6/2003 | Blakely et al. ................. 514/44 |

OTHER PUBLICATIONS

Okuda et al. (Nov. 22, 2002) "Single nucleotide polymorphism of the human high affinity choline transporter alters transpo rate." The Journal of Biological Chemistry 277(47): 45315-45322.*
Wells (Sep. 18, 1990) "Additivity of Mutational Effects in Proteins." Biochemistry 29(37): 8509-8517.*
Ngo et al. (Mar. 2, 1995) "The Protein Folding Problem and Tertiary Structure Prediction, Chapter 14: Computational Complexity Protein Structure Prediction, and the Levinthal Paradox" pp. 492-495.*
Bork (2000) "Powers and Pitfalls in Sequence Analysis: The 70% Hurdle." Genome Research 10:398-400.*
Skolnick and Fetrow (2000) "From gene to protein structure and function: novel applications of computational approaches in th genomic era." Trends in Biotech. 18(1): 34-39.*
Doerks et al., (Jun. 1998) "Protein annotation: detective work for function prediction." Trends in Genetics 14(6): 248-250.*
Smith and Zhang (Nov. 1997) "The challenges of genome sequence annotation or 'The devil is in the details'." Nature Biotechnology 15:1222-1223.*
Brenner (Apr. 1999) "Errors in genome annotation." Trends in Genetics 15(4): 132-133.*
Bork and Bairoch (Oct. 1996) "Go hunting in sequence databases but watch out for the traps." Trends in Genetics 12(10): 425-427.*
Apparsundaram et al. (Oct. 5, 2000) "Molecular Cloning of a Human, Hemicholinium-3-Sensitive Choline Transporter." Biochemical and Biophysical Research Communications 276(3): 862-867.*
Slotkin et al. (Aug. 1994) "Overexpression of the High Affinity Choline Transporter in Cortical Regions Affected by Alzheimer Disease." J. Clin. Invest. 94(2): 696-702.*
Verma and Somia (Sep. 18, 1997) "Gene therapy- promises, problems, and prospects." Nature 389: 239-241.*
Kaneda (Sep. 2001) "Gene Therapy: A Battle Against Biological Barriers" Current Molecular Medicine 1(4): 493-499.*
Eck and Wilson (1996) Chapter 5: "Gene-Based Therapy" Goodman & Gilmans's The Pharmacological Basis of Therapeutics 9th Ed. (pp. 77-100).*
"Nucleic Acid Hybridization- General Aspects" pp. 33-37 Roche website retrieved on May 12, 2004.*
NIH Division of Intramural Research "Nucleic Acid Hybridization" retrieved from NIH website on May 12, 2004.*
Jane et al. (Oct. 1998) "Vector development: a major obstacle in human gene therapy." Ann Med. 30(5): 413-5.*
Potter & Chang (Jun. 18, 1999) "Review—The use of immunosuppressive agents to prevent neutralizing antibodies against a transgene product." Ann N Y Acad Sci. 875: 159-74.*
Rozmahel et al. (Jul. 1997) "Incomplete rescue of cystic fibrosis transmembrane conductance regulator deficient mice by the human CFTR cDNA." Hum Mol Genet. 6(7): 1153-62.*
Kandel et al. Principles of Neural Science (Box 45-1 pp. 890-895), 1999.*
Busch et al. (Aug. 1998) "Human neurons express the polyspecific cation transporter hOCT2, which translocates monoamine neurotransmitters, amantadine, and memantine." Mol Pharmacol. 54(2): 342-52.*

(Continued)

*Primary Examiner*—Olga N. Chernyshev
(74) *Attorney, Agent, or Firm*—Robert Kinberg; Ann S. Hobbs; Venable LLP

(57) ABSTRACT

The present invention provides a protein having high-affinity choline transporter activity which is important physiologically, a gene encoding the protein, and a method of screening a material promoting the high-affinity choline transporter activity with the use of the same, and the like. By examining high-affinity choline uptake activity of $Na^+$-dependent transporter cDNA deduced from the genomic sequence of a nematode (*C. elegans*) in a *Xenopus* oocyte expression system, the cDNA (cho-1) of nematode high-affinity choline transporter is identified. Then the cDNA (CHT1) of rat high-affinity choline transporter is cloned from rat spinal cord by using the homology of a base sequence to this cDNA as an index. Similarly, the cDNA of human high-affinity choline transporter is cloned from human genome.

4 Claims, 10 Drawing Sheets

(1 of 10 Drawing Sheet(s) Filed in Color)

OTHER PUBLICATIONS

Modrek et al. (2000). A genomic view of alternative splicing. Nature Genetics, 30, 13-19.*

Kandel et al. Principles of Neural Science (Box 45-1 pp. 890-895), 1998.*

Busch et al. (Aug. 1998) "Human neurons express the polyspecific cation transporter hOCT2, which translocates monoamine neurotransmitters, amantadine, and memantine." Mol Pharmacol. 54(2): 342-52.*

Davis et al., "Basic Methods In Molecular Biology", Elsevier, pp. 1-3, (1986).

Haga, "Synthesis And Release Of [14C]Actylocholine In Synaptosomes", Journal Of Neurochemistry, vol. 18, pp. 781-798, (1971).

"Choline: High-Affinity Uptake By Rat Brain Synaptosomes", Science, vol. 178, pp. 626-628, (1972).

Haga et al., "Choline Uptake Systems Of Rat Brain Synaptosomes", Biochimica et Biophysica Acta, Elsevier Scientific Publishing Company, vol. 291, pp. 564-575, (1973).

Guyenet et al., "Inhibition By Hemicholinium-3 of [14C] Acetylcholine Synthesis And [3H]Choline High-Affinity Uptake In Rat Striatal Synaptosomes" Molecular Pharmacology, Academic Press, Inc., vol. 9, pp. 630-639, (1973).

Barker et al., "Comparative Studies of Substrates And Inhibitors Of Choline Transport And Choline Acetyltransferase", The Journal Of Pharmacology And Experimental Therapeutics, The Williams & Wilkins Co., vol. 192(1):86-94, (1975).

Kuhar et al., "Sodium-Dependent, High Affinity Choline Uptake", Journal Of Neurochemistry, vol. 30, pp. 15-21, (1978).

Tucek, "Regulation Of Acetylcholine Synthesis In The Brain", Journal Of Neurochemistry, International Society for Neurochemisty, vol. 44(1):11-24, (1985).

Happe et al., "High-Affinity Choline Transport Sites: Use of [3H]Hemicholinium-3 As A Quantitative Marker", Journal of Neurochemistry, International Society For Neurochemistry, vol. 60(4):1191-1201, (1993).

Kuhar et al., "Choline: Selective Accumulation by Central Cholinergic Neurons", Journal Of Neurochemistry, vol. 20, pp. 581-593, (1973).

Vickroy et al., "Reduced Density Of Sodium-Dependent [3H]Hemicholinium-3 Binding Sites In The Anterior Cerebral Cortex Of Rats Following Chemical Destruction Of The Nucleus *Basalis magnocellularis*", European Journal of Pharmacology, Elsevier Science Publishers B.V., vol. 102, pp. 369-370, (1984).

*ELEGANS*: Sequence to Biology, "Genome Sequence Of The Namatode *C. Elegans*: Aplatform For Investigating Biology", www.sciencemag.org, vol. 282, pp. 2012-2018, (1998).

Nelson, "The Family of Na+/C1-Neurotransmitter Transporters", Journal of Neurochemistry, International Society For Neurochemistry, vol. 71(5):1785-1803, (1998).

Hediger et al., "Expression Cloning And cDNA Sequencing Of The Na+/Glucose Co-Transporter", Nature, vol. 330, pp. 379-381, (1987).

Nikawa et al., "Primary Structure Of The Yeast Choline Transport Gene And Regulation Of Its Expression", The Journal Of Biological Chemistry, The American Society for Biochemistry And Molecular Biology, Inc., vol. 265(26):15996-16003, (1990).

Schloss et al., "The Putative Rat Choline Transporter Choti Transports Creatine And Is Highly Expressed In Neural And Muscle-Rich Tissues", Biochemical And Biophysical Research Communications, vol. 198(2):637-645, (1994).

Simon et al., "High Affinity Choline Uptake: Ionic And Energy Requirements", Journal Of Neurochemistry, vol. 27, pp. 93-99, (1976).

Vickroy et al., "Sodium-Dependent Hogh-Affinity Binding of [3H]Hemicholonium-3 In the Rat Brain: A Potentially Selective Marker For presynaptic Cholinergic Sites", Life Sciences, vol. 35, pp. 2335-2343, (1984).

Sandberg et al., "Characterization of [3H]Hemicholinium-3 Binding Associated With Neuronal Choline Uptake Sites In Rat Brain Membranes", Brain Research, Elsevier Science Publishers B.V., pp. 321-330, (1985).

Wurtman, "Choline Metabolishm As A Basis For The Selective Vulnerability Of Cholinergic Neurons", Elsevier Science Publishers Ltd, vol. 15(4):117-122, (1992).

Bissette, et al., "High Affinity Choline Transporter Status In Alzheimer's Disease Tissue From Rapid Autopsy", Annals New York Academy of Sciences, vol. 777, pp. 197-204, (1996).

Beeri et al., "Enhanced Hemicholinium binding And Attenuated Dendrite Branching In Cognitively Impaired Acetylcholinesterase-Transgenic Mice", Journal Of Neurochemistry, International Society For Neurochemistry, vol. 69(6):2441-2451, (1997).

"Continuous Cultures Of Fused Cells Secreting Antibody Of Predefined Specificity", Nature, vol. 256, pp. 495-497, (1975).

Kozbor et al., "The Production Of Monoclonal Antibodies From Human Lymphocytes", Immunology Today, Elsevier Biomedical Press, vol. 4(3):72-79, (1983).

Cole et al., "The EBV-Hybridoma Technique And Its Application To Human Lung Cancer", Monoclonal Antibodies And Cancer Therapy, Alan R. Liss, Inc., pp. 77-96, (1985).

Sambrook et al., "Molecular Cloning", A Laboratory Manual, Cold Spring Harbor Laboratory Press, vol. 1-3, 15 pages (2001).

Pietri-Rouxel et al., "The Biochemical Effect Of The Naturally Occurring Trp64-Arg Mutation On Human B3-Adrenoceptor Activity", Eur. J. Biochem., FEBS, vol. 247:1174-1179, (1997).

Takagi et al., "Ecpression Of A Cell Adhesion Molecule, Neuropilin, In The Developing Chick Nervous System", Developmental Biology, Academic Press, Inc., vol. 170, pp. 207-222, (1995).

Kawakami et al., "Developmentally Regulated Expression Of A Cell Surface Protein, Neuropilin, In The Mouse Nervous Ssytem", Journal of Neurobiology, vol. 29(1):1-17, (1996).

Kanai et al., "Primary Structure And Functional Characterization Of A High-Affinity Glutamate Transporter", Letters to Nature, vol. 360, pp. 467-471, (1992).

Cassata et al., "Rapid Expression Screening Of *Caenorhabditis elegans* Homeobox Open Reading Frames Using A Two-Step Polymerase Chain Reaction Promoter-gfp Reporter Construction Technique", Gene, Elsevier Science B.V., vol. 212, pp. 127-135, (1998).

Mello et al., "Efficient Gene Transfer In *C. Elegans*: Extrachromosomal Maintenance And Integration Of Transforming Sequences", The EMBO Journal, Ocford University Press, vol. 10(12):3959-3970, (1991).

Okuda et al., "Identification And Characterization Of The High-Affinity Choline Transporter", Nature Neuroscience, vol. 3(2):120-125, (2000).

Knipper et al., "Purification And Reconstitutio nOf The High Affinity Choline Transporter", Biochimica et Biophysica Acta, Elsevier Science Publishers B.V., vol. 1065, pp. 107-113, (1991).

Andresen et al., "Molecular Cloning, Physical Mapping And Expression Of The bet Genes Governing The Osmoregulatory Choline-Glycerine Betaine Pathway Of *Escherichia coli*", Journal Of General Microbiology, vol. 134, pp. 1737-1746, (1988).

Pocard et al., "Molecular Characterization Of The bet Genes Encoding Glycerine Betaine Synthesis In *Sinorhizobium meliloti* 102F34", Microbiology, vol. 143, pp. 1369-1379, (1997).

Knipper, M. et al., Isolation and Reconstitution of the High-Affinity Chkoline Carrier, Federation of European Biochemical Societies Letters, vol. 245, No. 1-2, 1989, pp. 235-237.

Database EMBL (Online)Nov. 23, 1998, Burton J., *Caenorhabditis elegans* cosmid C48D1, complete listing: Database accession No. Z81049 X-002235196.

* cited by examiner

Fig. 4

```
CHT1   MPFHEGVAITFYLLIPVGIWAAWKFKNS----GNAEERSEALVVGGRMIGLLVGGF   56
cht-1  -MADLGVAIVFYLLIVVGIWAGRKSKSSKELESAGAAEEWMAGRNIGTLVGIF      59
              I
CHT1   TMTATWVGGGYINGTAEAVYGPGCGLAWAQAPFGYSLSLLGGLFFAKPMRSKGYVTMLD  116
cht-1  TMTATWVGGAYINGTAEALYNG--GLLGCQAPVGYASLMGGLLFAKKMRESGYVTMLD   117
                                  II
CHT1   PFQSIYGKRYGGLLVSPALMGEVFWAAAISSALGATSSVIDDDVNISVISSALIAAHYT  176
cht-1  PFQSKYGQRIGGLMYVPALLGETFWTAAISSALGATSSVIGDVNASVTSACIAMRYT    177
                   III                                    IV
CHT1   VGGLYSVAYTDVVQLFCIFYGLWVSVPFAISHPVVTDIGFTAVHAKYQSPWMGTIES-V  235
cht-1  FTGGYYLVAYTDVVQLFCIFIGLWYCVPAAMVHDGAKDISRNAG------DWIGEIGGFK 231
                   V
CHT1   EVYTWLDNLLLMLGGIPWQAYFQRVLSSSSATYAQVLSFLAAFGCYMALPAICIGAIG   295
cht-1  ETSLWIDCYLLLMGGIPWQVYFQRVLSSKTAHGAQTLSFVAGVGCLMATPPALIGAIA   291
              VI                       VII
CHT1   ASTDWNQTAYGFPDPKTKEEAD------MILPIVLQYLCPVYISFIGLGAVSAAVMSSAD 349
cht-1  RNTDWRMTDYSPWNNGTKVESIPPDKRNMWPLVIQYLTPRWVAFIGLGAVSAAVMSSAD   351
                                                    VIII
CHT1   SSILSASSMFARNIYQLSFRQFASEKEIWWVMRIIVFVFGASATAMALLTKMVYGLWYLS 409
cht-1  SSVLSAASMFANIMKLFTRPFASEKEVIIVMRIAFICVGIMATIMALTIQSEYGLWYLC   411
                                          IX
CHT1   SDLVYIIFPQLLCVLETKGINTYGAVAGYIFGLFLRITGGEPYMYLQPLIFYPGYYPDK  469
cht-1  SDLVYILFPQLLCVVYVPRSNTYGSLAGYAVGLVLRIIGGEPLVSLPAIHYPMYT--D   469
         X                     XI
CHT1   NGIYNQRFPFKTLSMVISFFTNICVSYLAKYLFESGTLPPKLDIEDAVVSR---HSEENM 526
cht-1  G---VQYFPFRTTAMSSMATIYIVSIQSEKLFKSGRLSPWDVMGCVVNIPIDHVPLPS   526
                         XII
CHT1   DKTILVRNENIKLNELAPVKPRQSLTLSSTFINKEALLDVDSSPEGSGTEDNLQ       580
cht-1  DVSFAVSSE--TLNMKAPNGTPAPVHPNQQPSDENILLHPYSDQSYYSTNSN--       576
```

HIGH-AFFINITY CHOLINE TRANSPORTER

TECHNICAL FIELD

This invention relates to a protein having high-affinity choline transporter activity, a gene encoding said protein and the use of the same.

PRIOR ART

The autonomic nervous system which spreads to organs throughout a body and regulates the most basic functions of living organism including energy metabolism, circulation, respiration and reproduction along with endocrine system, is classified into the sympathetic and parasympathetic nervous systems. All autonomic nerve fibers excluding postganglionic fibers of the sympathetic nerve, motor nerve fiber, and sudoriferous gland/blood vessel dilative fiber in the sympathetic nerve are cholinergic, and acetylcholine is vital for the function of the autonomic nerve and the motor nerve. It has been known that the cholinergic neuron, being observed also in the brain, is important for recognizing function of the brain and that it degenerates after the onset of Alzheimer's disease. In the cholinergic neuron, because of lack of biosynthetic ability for choline, choline, an acetylcholine decomposition product, is taken up into a cell by a high-affinity choline transporter at the presynaptic terminals to be reused for synthesizing acetylcholine. The high-affinity choline uptake is a rate-limiting step for acetylcholine synthesis and is presumed to regulate the efficiency of synaptic transmission (J. Neurochem. 18, 781-798, 1971, Science 178, 626-628, 1972, Biochem. Biophys. Acta 291, 564-575, 1973, Mol. Pharmacol. 9, 630-639, 1973, J. Pharmacol. Exp. Ther. 192, 86-94, 1975, J. Neurochem. 30, 15-21, 1978, J. Neurochem. 44, 11-24, 1985, J. Neurochem. 60, 1191-1201, 1993, J. Neurochem. 20, 581-593, 1973, Eur. J. Pharmacol. 102, 369-370, 1984). To date, most of cDNAs of transporters for major neurotransmitters have been isolated, however, a cDNA of the high-affinity choline transporter, which is physiologically important, has not been identified.

DISCLOSURE OF THE INVENTION

So far, the existence of a protein being localized in the cholinergic neuron and having a function of taking up choline, a precursor of acetylcholine, into a cell has been expected, but molecular properties of said protein, a high-affinity choline transporter, have been unknown. An object of the present invention is to provide a physiologically important protein having the high-affinity choline transporter activity, a gene which encodes the protein, and a screening method of a high-affinity choline transporter activity promoter using the protein, the gene and the like.

The inventors have conducted intensive study to attain the above-mentioned object: with information of genomic project (Science 282, 2012-2018, 1998), $Na^+$-dependent transporter cDNAs being expected from the genomic sequence of a nematode (*C. elegans*) were cloned one by one, and the high-affinity choline uptake activity of each cDNA was examined in the oocyte expression system of *Xenopus*, and the cDNA of nematode high-affinity choline transporter (cho-1) was identified on the basis of the above examination, then homologous molecules (CHT1) were cloned from rat spinal cord by using the homology of a base sequence to the cDNA as an index. This CHT1 had no homology to neurotransmitter transporters (J. Neurochem. 71, 1785-1803, 1998), but had 20 to 25% homology to molecules which belong to $Na^+$-dependent glucose transporter family (Nature 330, 379-381, 1987).

Northern blot analysis revealed that transcripts of CHT1 were confirmed only in spinal cord, basal forebrain, corpus striatum and brain stem, and CHT1 seemed to be expressed in cholinergic neurons. Accordingly, CHT1 was expressed in oocytes of *Xenopus*. As a result, choline uptake activity that is $Na^+$-dependent and completely inhibited by hemicholinium-3 was observed. These results indicate that CHT1 has high-affinity choline transporter activity. Further, the inventors have cloned choline transporter cDNAs derived from a human and from a mouse, and determined their base sequences, and have confirmed that their expression products have high-affinity choline uptake activity. The present invention has thus completed.

The present invention relates to a gene which encodes a protein having high-affinity choline transporter activity, a gene which encodes a protein (a) or (b) described below; (a) a protein comprising an amino acid sequence represented by Seq. ID No. 2, (b) a protein comprising an amino acid sequence where one or a few amino acids are deficient, substituted or added in the amino acid sequence represented by Seq. ID No.2, and having high-affinity choline transporter activity, DNA containing a base sequence represented by Seq. ID No. 1 or its complementary sequence and a part or a whole of these sequences, DNA derived from a nematode which hybridizes with DNA comprising a gene according to the above under a stringent condition, and encodes a protein having high-affinity choline transporter activity, a gene which encodes a protein (a) or (b) described below; (a) a protein comprising an amino acid sequence represented by Seq. ID No. 4, (b) a protein comprising an amino acid sequence where one or a few amino acids are deficient, substituted or added in the amino acid sequence represented by Seq. ID No.4, and having high-affinity choline transporter activity, DNA containing a base sequence represented by Seq. ID No. 3 or its complementary sequence and a part or a whole of these sequences, DNA derived from a rat which hybridizes with DNA comprising a gene according to the above under a stringent condition, and encodes a protein having high-affinity choline transporter activity, a gene which encodes a protein (a) or (b) described below; (a) a protein comprising an amino acid sequence represented by Seq. ID No. 6, (b) a protein comprising an amino acid sequence where one or a few amino acids are deficient, substituted or added in the amino acid sequence represented by Seq. ID No.6, and having high-affinity choline transporter activity, DNA containing a base sequence represented by Seq. ID No. 5 or its complementary sequence and a part or a whole of these sequences, DNA derived from a human which hybridizes with DNA comprising a gene containing Seq ID No. 5 or its complementary sequence or a portion of either under a stringent condition, and encodes a protein having high-affinity choline transporter activity, a gene which encodes a protein (a) or (b) described below; (a) a protein comprising an amino acid sequence represented by Seq. ID No. 8, (b) a protein comprising an amino acid sequence where one or a few amino acids are deficient, substituted or added in the amino acid sequence represented by Seq. ID No.8, and having high-affinity choline transporter activity, DNA containing a base sequence represented by Seq. ID No. 7 or its complementary sequence and a part or a whole of these sequences, and DNA derived from a mouse which hybridizes with DNA comprising a gene comprising a base sequence represented by Seq ID No. 7 or its complementary sequence or a portion of either under a stringent condition, and encodes a protein having high-affinity choline transporter activity.

The present invention also relates to a protein having high-affinity choline transporter activity, a protein comprising an amino acid sequence represented by Seq. ID No. 2, a protein comprising an amino acid sequence where one or a few amino acids are deficient, substituted or added in the amino acid sequence represented by Seq. ID No.2, and having nematode high-affinity choline transporter activity, a protein comprising an amino acid sequence represented by Seq. ID No. 4, a protein comprising an amino acid sequence where one or a few amino acids are deficient, substituted or added in the amino acid sequence represented by Seq. ID No.4, and having rat high-affinity choline transporter activity, a protein comprising an amino acid sequence represented by Seq. ID No. 6, a protein comprising an amino acid sequence where one or a few amino acids are deficient, substituted or added in the amino acid sequence represented by Seq. ID No.6, and having human high-affinity choline transporter activity, a protein comprising an amino acid sequence represented by Seq. ID No. 8, and a protein comprising an amino acid sequence where one or a few amino acids are deficient, substituted or added in the amino acid sequence represented by Seq. ID No.8, and having mouse high-affinity choline transporter activity.

The present invention further relates to a fusion protein being constructed by expressing a cDNA encoding fusion proteins of a protein having high-affinity choline transporter activity and a marker protein and/or a peptide tag, the fusion protein according to the above, wherein the protein having high-affinity choline transporter activity has nematode high-affinity choline transporter activity as described as above, the fusion protein according to the above, wherein the protein having high-affinity choline transporter activity has rat high-affinity choline transporter activity, the fusion protein according to the above, wherein the protein having high-affinity choline transporter activity has human high-affinity choline transporter activity, and the fusion protein according to the above, wherein the protein having high-affinity choline transporter activity has mouse high-affinity choline transporter activity.

The present invention still further relates to an antibody which specifically binds to a protein having high-affinity choline transporter activity, the described antibody wherein the protein having high-affinity choline transporter activity has nematode high-affinity choline transporter activity, the described antibody, wherein the protein having high-affinity choline transporter activity has rat high-affinity choline transporter activity, the described antibody, wherein the protein having high-affinity choline transporter activity has human high-affinity choline transporter activity, the described antibody, wherein the protein having high-affinity choline transporter activity has mouse high-affinity choline transporter activity, and the described antibody according to any of the above, wherein the antibody is a monoclonal antibody.

The present invention also relates to a host cell containing an expression system which can express a protein having high-affinity choline transporter activity, the host cell, wherein the protein having high-affinity choline transporter activity has nematode high-affinity choline transporter activity, the host cell wherein the protein having high-affinity choline transporter activity has rat high-affinity choline transporter activity, the host cell, wherein the protein having high-affinity choline transporter activity has human high-affinity choline transporter activity, and the host cell, wherein the protein having high-affinity choline transporter activity has mouse high-affinity choline transporter activity.

The present invention further relates to a non-human animal in which function of a gene which encodes a protein having high-affinity choline transporter activity is deficient or overexpresses on its chromosome, the non-human animal, wherein the protein having high-affinity choline transporter activity has nematode high-affinity choline transporter activity, the non-human animal, wherein the protein having high-affinity choline transporter activity has rat high-affinity choline transporter activity, the non-human animal, wherein the protein having high-affinity choline transporter activity has human high-affinity choline transporter activity, the non-human animal wherein the protein having high-affinity choline transporter activity has mouse high-affinity choline transporter activity, and the non-human animal according to any of the above, wherein the non-human animal is a mouse or a rat.

The present invention still further relates to a preparing method of a cell having high-affinity choline transporter activity characterized in introducing the gene or the DNA as described above into a cell whose function of a gene which encodes a protein having high-affinity choline transporter activity is deficient on its chromosome, the preparing method of a cell having high-affinity choline transporter activity, wherein the cell having high-affinity choline transporter activity is integrated with the gene or the DNA as described above in its chromosome, and stably shows high-affinity choline transporter activity, and a cell having high-affinity choline transporter activity being obtainable by the preparing method of a cell having high-affinity choline transporter activity as described.

The present invention also relates to a screening method of a promoter or a suppressor of high-affinity choline transporter activity characterized in measuring/evaluating high-affinity choline transporter activity of the protein having high-affinity choline transporter activity according to the above in the presence of a subject material, a screening method of a promoter or a suppressor of high-affinity choline transporter activity, or of high-affinity choline transporter expression characterized in comprising the steps of: a cell membrane or a cell which expresses a protein having high-affinity choline transporter activity is cultivated in vitro in the presence of a subject material; the activity and/or the expression amount of a protein having high-affinity choline transporter activity in the cell membrane or the cell is measured/evaluated, the screening method of a promoter or a suppressor of high-affinity choline transporter activity, or of high-affinity choline transporter expression, wherein the cell membrane or the cell which expresses a protein having high-affinity choline transporter activity is the host cell containing an expression system which can express a protein having high-affinity choline transporter activity according to any of the above, or is the cell having high-affinity choline transporter activity according to the above, the screening method of a promoter or a suppressor of high-affinity choline transporter activity, or of high-affinity choline transporter expression according to the above, wherein the protein having high-affinity choline transporter activity is a recombinant protein, a screening method of a promoter or a suppressor of high-affinity choline transporter activity, or of high-affinity choline transporter expression characterized in comprising the steps of: a cell obtained from the non-human animal according to any of the above is cultivated in vitro in the presence of a subject material; the activity and/or the expression amount of a protein having high-affinity choline transporter activity in the cell is measured/evaluated, a screening method of a promoter or a suppressor of high-affinity choline transporter activity, or of high-affinity choline transporter expression characterized in administering a subject material to a non-human animal and then evaluating the activity and/or the expression amount of a protein having high-affinity choline transporter activity, a screening method of a promoter or a suppressor of high-affinity choline transporter activity, or of high-affinity choline transporter expression characterized in administering a subject material to a non-human animal whose function of a gene encoding a protein having high-affinity choline transporter activity is deficient or overexpresses on its chromosome, and then evaluating the activity and/or the expression amount of a protein having high-affinity choline transporter activity, a screening method of a promoter or a suppressor of high-affinity choline transporter activity, or of high-affinity choline transporter expression characterized in administering a subject material to a non-human animal whose function of a gene encoding a protein having high-affinity choline transporter activity is deficient or overexpresses on its chromosome, and then evaluating the activity and/or the expression amount of a protein having high-affinity choline transporter activity in comparison with the case using wild-type non-human animal, and the screening method of a promoter or a suppressor of high-affinity choline transporter activity, or of high-affinity choline transporter expression according to any of the above, wherein the non-human animal is a mouse or a rat.

The present invention further relates to a material which promotes activity or expression of a protein having high-affinity choline transporter activity being obtainable by the screening method as described above, a material which suppresses activity or expression of a protein having high-affinity choline transporter activity being obtainable by the screening method according to the above, a medical constituent characterized in being used for a medical treatment for a patient who needs elevation of the activity or enhancement of the expression of a high-affinity choline transporter, and containing the protein according to any of the above, and/or the material which promotes activity or expression of a protein having high-affinity choline transporter activity according to the above as an active component, and a medical constituent characterized in being used for medical treatment for a patient who needs suppression of the activity or the expression of a high-affinity choline transporter, and containing the protein according to the above, and/or the material which suppresses the activity or the expression of a protein having high-affinity choline transporter activity according to the above as an active component.

The present invention still further relates to a diagnostic method for diseases relating to the expression or the activity of a high-affinity choline transporter characterized in comparing a DNA sequence encoding a high-affinity choline transporter in a sample to a DNA sequence encoding the protein as described above, a diagnostic probe for Alzheimer's disease comprising a whole or a part of an antisense strand of DNA or RNA encoding the protein as described above, and a diagnostic drug for Alzheimer's disease characterized in containing the diagnostic probe as described above and/or the antibody as described above.

BRIEF EXPLANATION OF THE DRAWINGS

The patent or application file contains at least one drawing executed in color. Copies of this patent or patent application publication with color drawing(s) will be provided by the Office upon request and payment of the necessary fee.

FIG. 4 is a view showing amino acid sequences of rat CHT1 and nematode CHO-1 of the present invention respectively.

BEST MODE FOR CARRYING OUT THE INVENTION

The cDNA of nematode high-affinity choline transporter of the present invention, being described in Seq. ID No. 1, can be obtained by injecting each cRNA prepared from candidate full-length cDNAs, which are expected as a member of $Na^+$-dependent transporter family according to *C. elegans* genome project, into oocytes of *Xenopus*, and examining the uptake of choline. The high-affinity uptake of choline in brain synaptosomes of mammals was completely inhibited by 1 μM hemicholinium-3 (HC3) (Ki=10-100 nM), while the low-affinity uptake of choline, which is distributed in every cells, was inhibited only by HC3 with higher concentration (Ki=50 μM). Therefore, the sensitivity to 1 μM HC3 can be used as criteria of high-affinity choline uptake during the process. For example, it is possible to confirm the identification, the expression, and the localization of an object gene from the candidate cDNA of a nematode (*C. elegans*) as follows.

Figure 1:
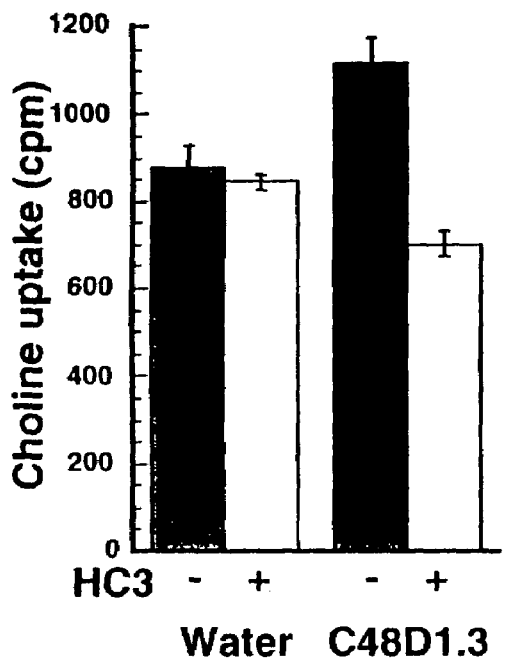
FIG. 1 is a view showing the result of [$^3$H] choline uptake of oocytes from *Xenopus* of the present invention being injected with nematode cho-1 (C48D1.3 cRNA) or water.
Figure 2:
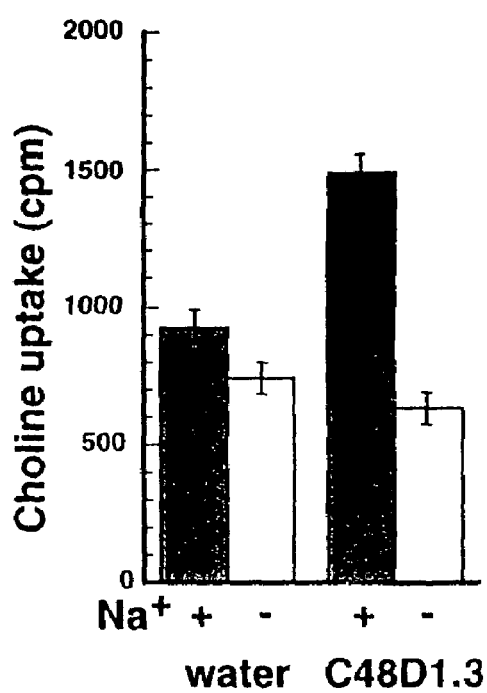
FIG. 2 is a view showing the result of the effect of $Na^+$ on choline uptake of oocytes from *Xenopus* of the present invention being injected with nematode cho-1 (C48D1.3 cRNA) or water.
Figure 3:
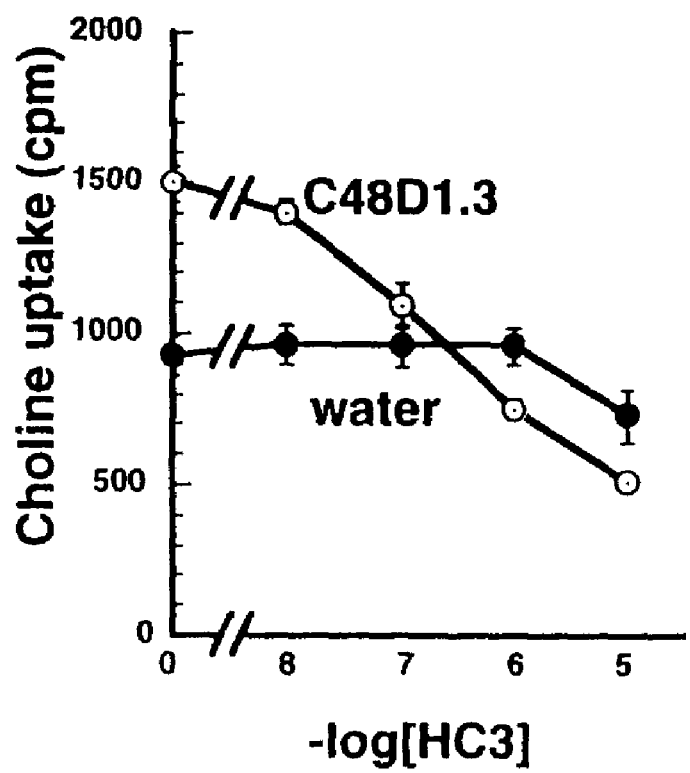
FIG. 3 is a view showing the result of the HC3-induced inhibition of choline uptake of oocytes from *Xenopus* of the present invention being injected with nematode cho-1 (C48D1.3 cRNA) or water.

It has been found that cDNA corresponding to the gene expected as C48D1.3 promotes significant choline uptake, being inhibited by 1 μM HC3, in the high-affinity choline uptake process. FIG. 1 shows the result of [$^3$H] choline uptake of oocytes from *Xenopus* being injected with C48D1.3 cRNA or water. In FIG. 1, the closed and the open columns indicate choline uptake in the absence or the presence of 1 μM HC3 respectively, and each column is shown by mean ±SEM (n=6 to 8 oocytes). FIG. 2 shows the effect of $Na^+$ on the choline uptake, and the closed columns indicate choline uptake measured in the standard solution ($[Na^+]$=100 mM), the open columns indicate choline uptake in the absence of $Na^+$ ($Na^+$ was substituted with $Li^+$). In addition, FIG. 3 shows the inhibition of choline uptake induced by HC3. Based on the above-mentioned FIGS. 2 and 3, it is presumed that the uptake is $Na^+$-dependent, and that Ki of HC3 is 50 nM. The cDNA clone was designated as cho-1 (high-affinity choline transporter-1).

By comparing a base sequence of cDNA and that of genome, cho-1 gene was found to comprise 9 exons. A protein expected from a base sequence of cDNA of cho-1 includes 576 amino acid residues (see FIG. 4), and this protein, being represented by Seq. ID No. 2, can be constructed by a usual method. When the available data base was searched, the amino acid sequences of cho-1 showed weak, but significant homology to members of $Na^+$-dependent glucose transporter family. Hydrophobic analysis and comparison to other transporters suggest that there is a twelve-transmembrane region (see FIG. 7).

Figure 5:
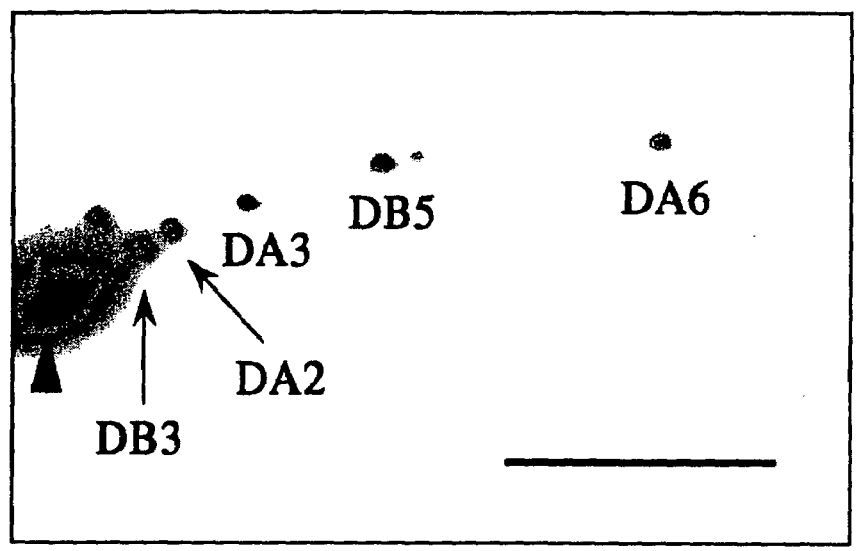
FIG. 5 is a view showing the distribution of neurons expressing cho-1::gfp of the present invention in the nervous system of nematode.

Then, in order to identify cells expressing cho-1 in the nervous system of a nematode (*C. elegans*), a gene of a green fluorescent protein (GFP) fused with a region 5.1 kb upstream from cho-1 gene was introduced into a nematode, and distribution of neurons expressing cho-1::gfp was examined. A photograph of L1 larva possessing cho-1::gfp reporter DNA at the outside of chromosome is shown as FIG. 5 (scale bar; 50 μm). In FIG. 5, the arrowhead indicates nerve ring. In the ventral nerve cord, GFP is expressed only in cholinergic motor nerve, however, some of DA, DB nerve cells do not express GFP owing probably to deficiency of reporter DNA at the outside of chromosome. It supports the idea that cho-1 is a high-affinity choline transporter of the cholinergic neuron.

The cDNA of rat high-affinity choline transporter of the present invention, being described in Seq. ID No. 3, can be prepared, for example, by a method comprising the steps of: paying attention to cho-1 homologous molecules of vertebrates and searching data base with amino acid sequences expected from cho-1, and identifying one candidate (GenBank accession number: AQ 316435) in human genomic survey sequence (GSS); amplifying cDNA fragments from rat spinal cord cDNA by PCR with degenerate primers on the basis of homology of base sequences between the human genome DNA and cho-1; screening rat spinal cord cDNA library with this fragment, and a positive cDNA clone was obtained. A protein with 580 amino acid residues showing 51% identity and 70% similarity to cho-1 was expected from the base sequence of the longest reading frame (see FIG. 4). This rat cDNA clone was designated as CHT1. In FIG. 4, each amino acid sequence of rat CHT1 and nematode CHO-1 is shown, and the identical and the similar residues are indicated on a black ground and a gray ground respectively. The expected transmembrane region I-XII is underlined. This protein represented by Seq. ID No. 4 can be constructed by a usual method.

Figure 6:
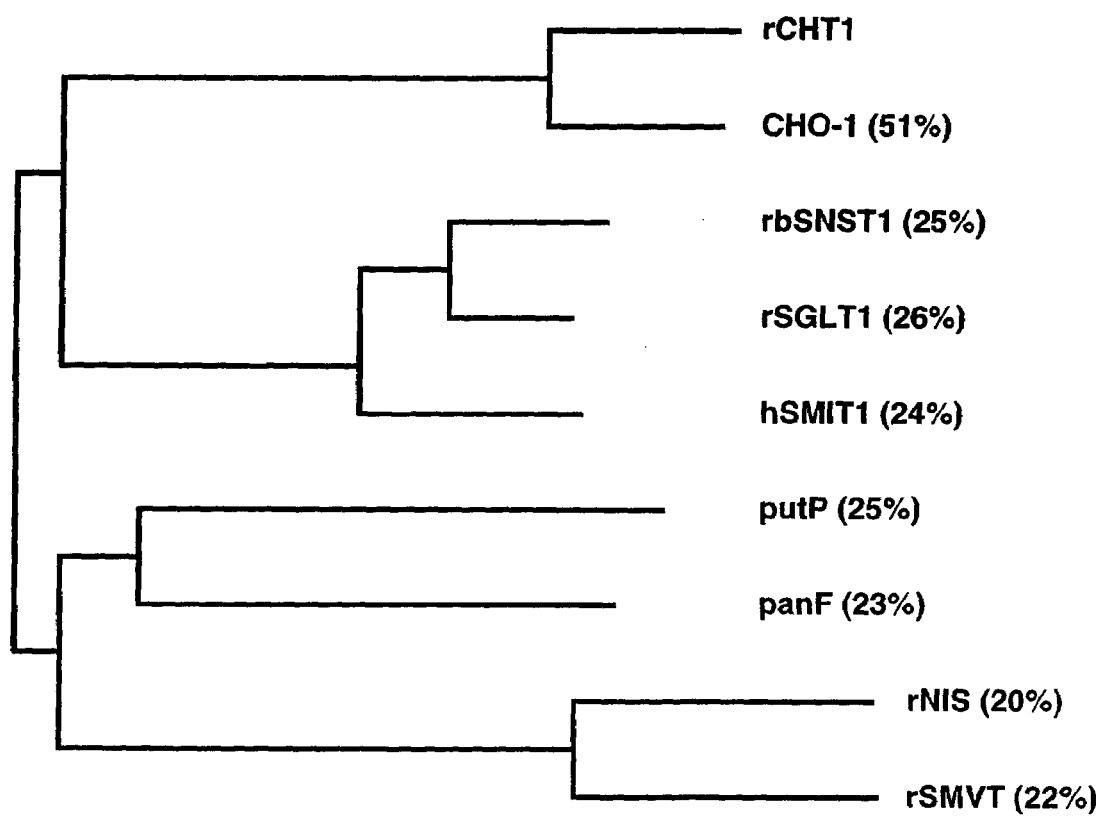
FIG. 6 is a view showing the phylogenetic tree of $Na^+$-dependent glucose transporter family.

The above-mentioned amino acid sequence of CHT1 is significantly homologous to members of $Na^+$-dependent glucose transporter family (20 to 25%). The phylogenetic tree of $Na^+$-dependent glucose transporter family made by neighbor-joining method using a program CLUSTALW of National Institute of Genetics (Mishima, Japan) is shown in FIG. 6. In FIG. 6, the percentage of the identical amino acids, being contained in each protein, to rat CHT1 is shown on the right side. On the other hand, no homology was observed to a yeast choline transporter (J. Biol. Chem. 265, 15996-16003, 1990), a creatine transporter which had been originally reported as a high-affinity choline transporter (Biochem. Biophys. Res. Commun. 198, 637-645, 1994), and other neurotransmitter transporters.

Figure 7:
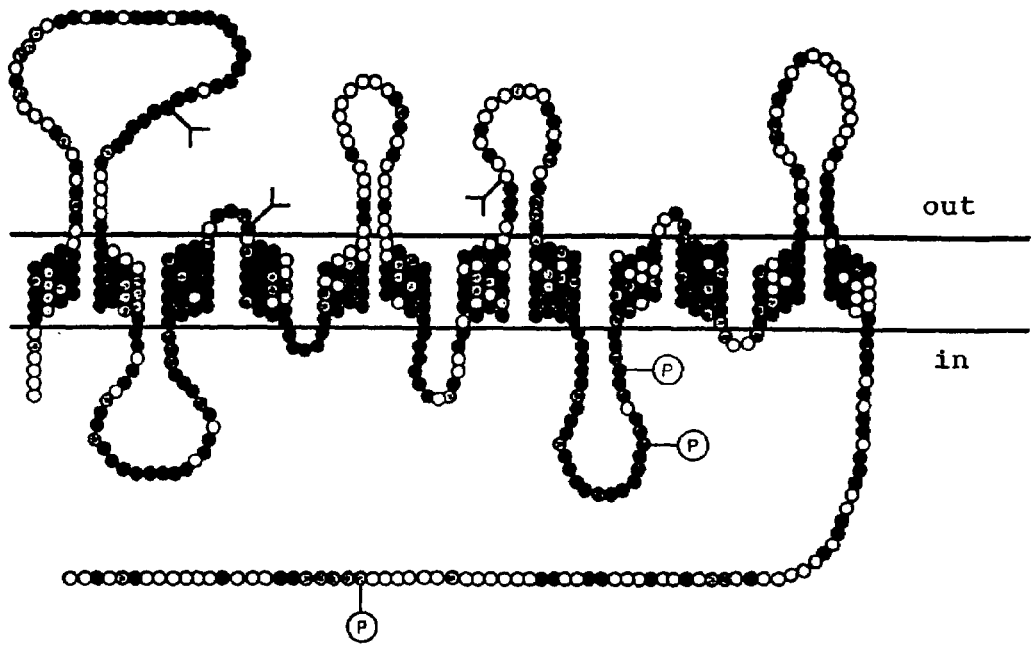
FIG. 7 is a view showing an expected topology of rat CHT1 of the present invention.

The expected topology of CHT1 is thought to be the same as that of nematode CHO-1 fundamentally. FIG. 7 shows the expected topology of rat CHT1. In FIG. 7, the closed circles indicate the identical residues, the shadowed circles indicate highly conserved residues, and open circles indicate nonsimilar residues. The offshoots indicate the expected glycosylation sites. P among the circles shows the expected parts of phosphorylation induced by protein kinase C.

Figure 8:
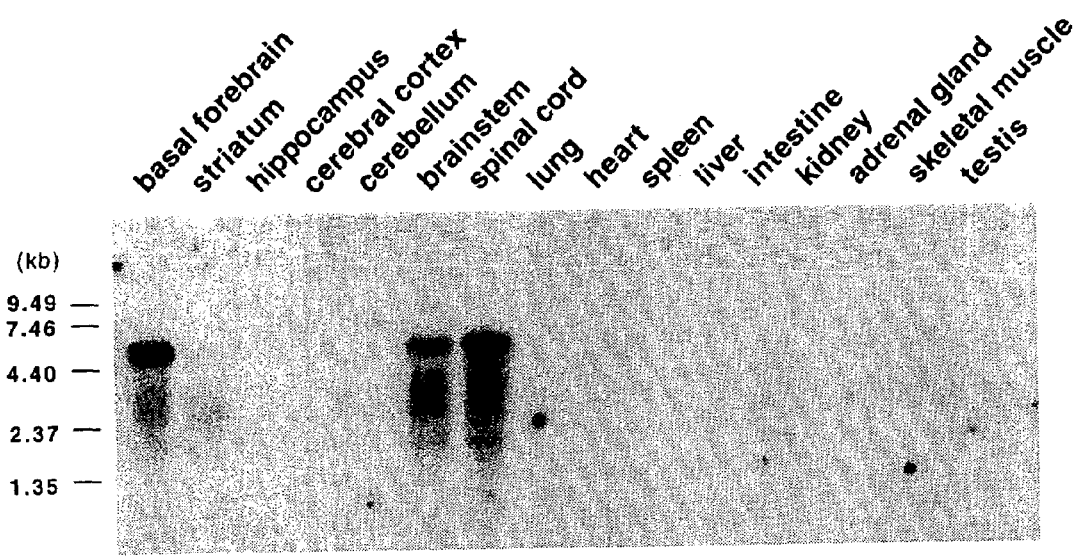
FIG. 8 is a view showing the result of Northern blot analysis of CHT1 mRNA transcript in rat tissue of the present invention.

Next, the distribution of CHT1 mRNA expression was examined by Northern blot analysis and in situ hybridization. The expression of transcripts with the length of about 5 kb was confirmed by Northern blot analysis of various tissues of rats. FIG. 8 shows the result of Northern blot analysis of mRNA transcript of CHT1 in rat tissue, and the length of RNA standard (0.24 to 9.5 kb; GIBCO BRL) is exhibited on the left side. As shown in FIG. 8, an abundance of transcripts were confirmed in basal forebrain, brain stem and spinal cord, and a little of those were confirmed in corpus striatum. These tissues are known to contain cholinergic neurons. On the other hand, no transcript was observed in other regions of the brain or in tissues of non-nervous systems.

Figure 9:
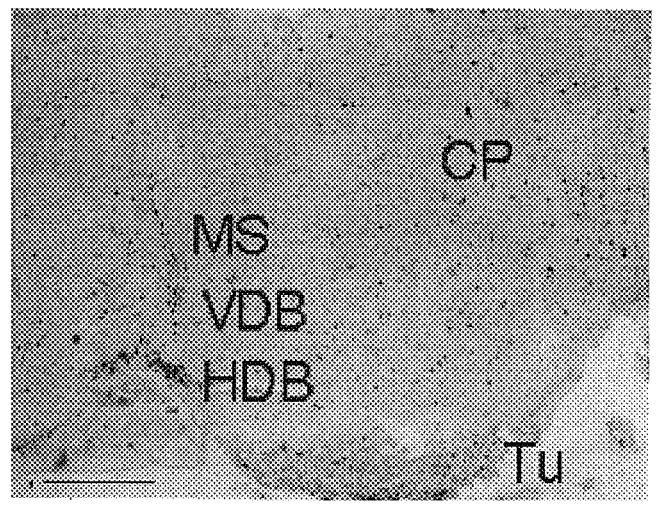
FIG. 9 is a view showing the result of in situ hybridization analysis of CHT1 transcript in a rat brain of the present invention.
Figure 10:
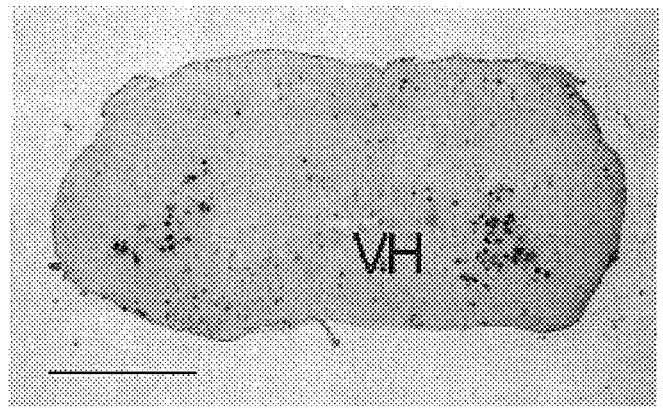
FIG. 10 is a view showing the result of in situ hybridization analysis of CHT1 transcript in a spinal cord of the present invention.

Consistent with these results, in situ hybridization confirmed the expression of CHT1 mRNA in cell groups of main cholinergic neurons including corpus striatum, cell population in basal forebrain and vental horn in spinal cord. FIGS. 9 and 10 (scale bar; 1 mm) show micrographs of sections in bright-field, which were hybridized with a cRNA probe of an antisense labeled by digoxigenin. These micrographs relate to in situ hybridization analysis of CHT1 transcripts in rat brain and spinal cord. FIG. 9 indicates that mRNA transcripts of CHT1 were detected in vertical and horizontal limbs of the diagonal band (VDB, HDB), medial septal nucleus (MS), caudate and putamen (Cpu), and olfactory tubercle (Tu). FIG. 10 indicates that the expression was observed in ventral horn (VH) in spinal cord. Further, the adjacent section hybridized with a probe of vesicle acetylcholine transporter showed essentially same distribution. This expression distribution is essentially same as the reported distribution of cholineacetyl group transferase or vesicle acetylcholine transporter. These results show that the expression of CHT1 mRNA is limited to cholinergic neurons.

Figure 11:
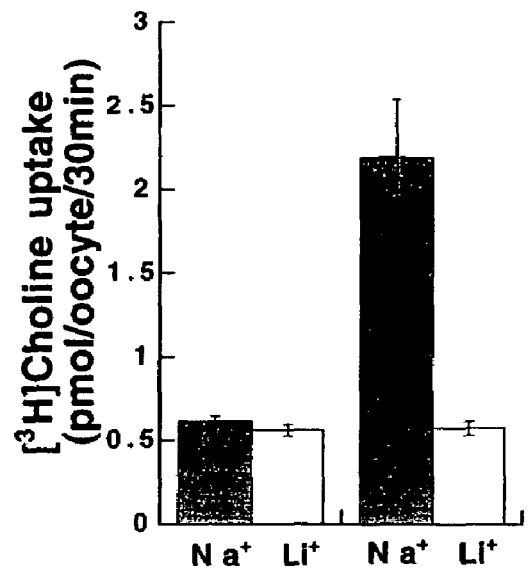
FIG. 11 is a view showing the result of [$^3$H] choline uptake of oocytes from *Xenopus* of the present invention being injected CHT1 cRNA of the present invention or water.
Figure 12:
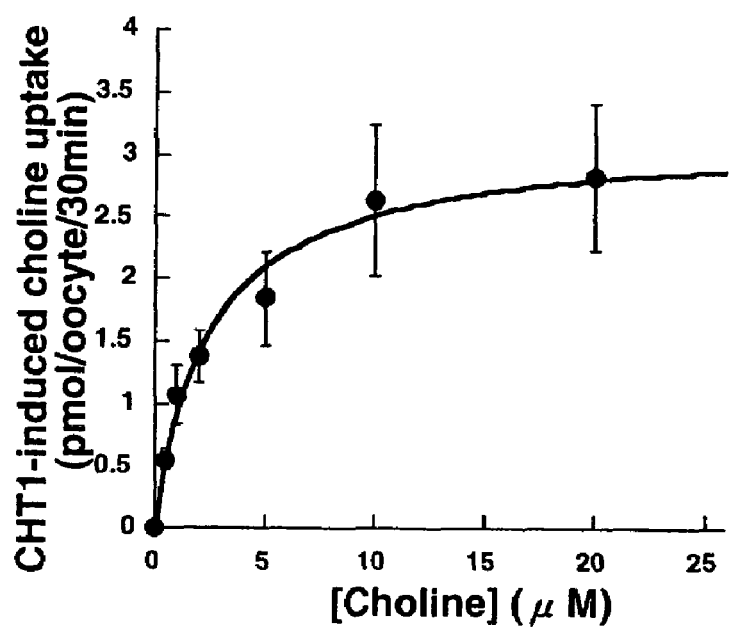
FIG. 12 is a view showing the effect of choline concentration on choline uptake in CHT1 of the present invention.

Next, choline uptake of CHT1 was examined by using oocytes of *Xenopus*. The choline uptake of the oocytes injected with CHT1 cRNA was 2 times to 4 times more than that of controls injected with water. FIG. 11 shows the result of ($^3$[H] choline uptake of oocytes of *Xenopus* injected with CHT1 cRNA or water. In FIG. 11, the open and the closed columns respectively indicate choline uptake in the standard solutions containing 100 mM NaCl or LiCl, and each column is shown by mean ±SEM (n=6 to 8 oocytes). The effect of choline concentration on choline uptake is shown in FIG. 12. In FIG. 12, choline uptake of oocytes injected with water was subtracted from that of oocytes injected with cRNA in order to figure out CHT1-induced choline uptake, and the choline uptake was fitted to Michaelis-Menten curve. As shown in FIG. 12, choline uptake of CHT1 saturated when increasing choline concentration (Km=2.2±0.2 μM, n=3). The Km of endogenous choline uptake of control is higher than 10 μM.

Figure 13:
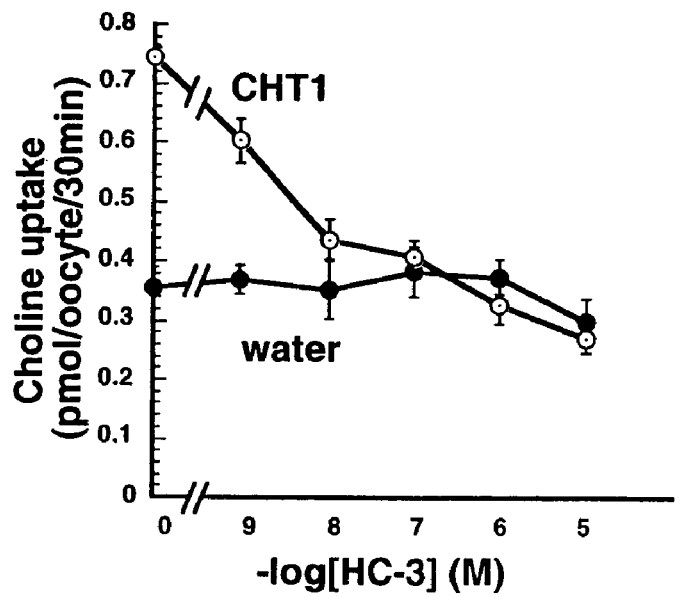
FIG. 13 is a view showing the result of HC3-induced inhibition of choline uptake of CHT1 of the present invention.
Figure 14:
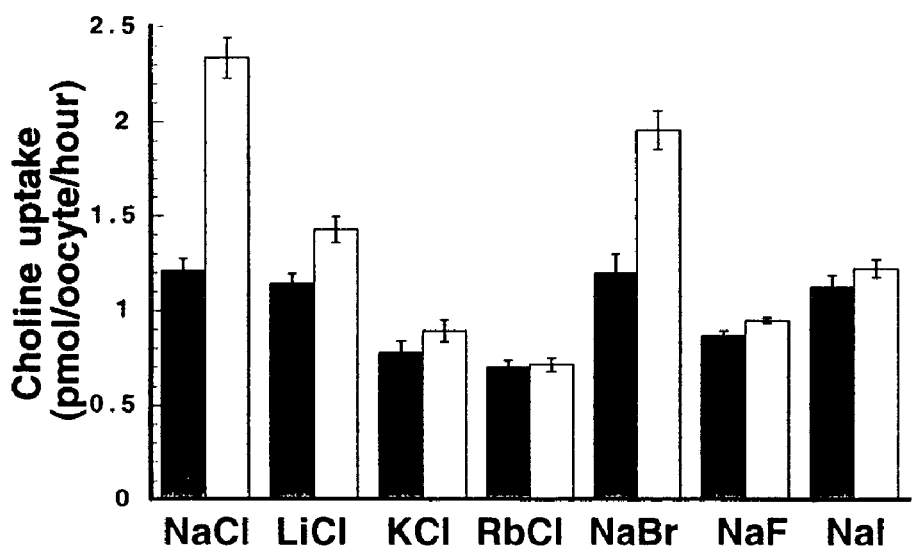
FIG. 14 is a view showing the result of $Na^+$- and $Cl^-$-dependent choline uptake of CHT1 of the present invention.

Then, the result of HC3-induced inhibition of choline uptake is shown in FIG. 13. FIG. 13 indicates that choline uptake of CHT1 is completely inhibited by 0.1 μM HC3 (Ki=2-3 nM), whereas 10 μM HC3 induced only slight inhibition in control. As shown in FIG. 14, ion-dependency of choline uptake of CHT1 was examined and found to be $Cl^-$-dependent as well as $Na^+$-dependent. The closed and the open columns indicate choline uptake of oocytes injected with water and with cRNA respectively (100 mM NaCl in the standard solution is substituted with 100 mM of each salt) shown in the figure. These results indicate that CHT1 has the characteristics expected from high-affinity choline uptake in brain synaptosomes (high-affinity to choline, high sensitivity to HC3, and $Na^+$—$Cl^-$-dependency) (J. Neurochem. 27, 93-99, 1976).

Figure 15:
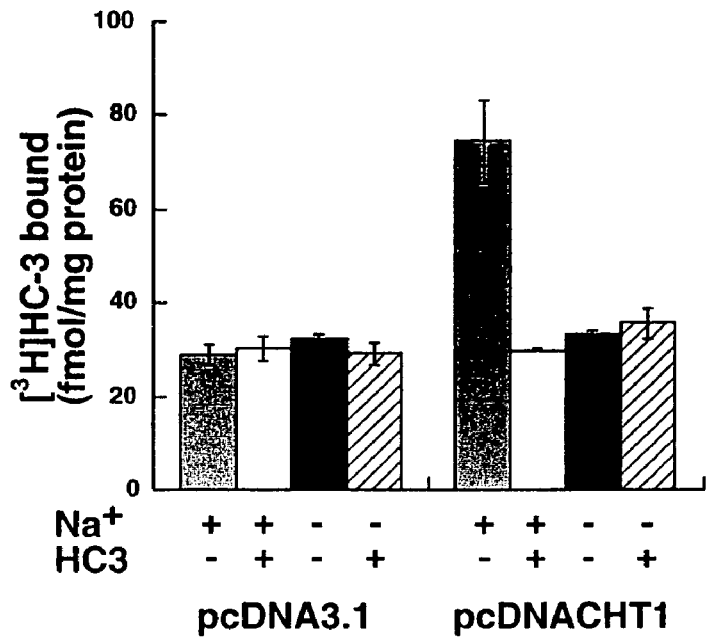
FIG. 15 is a view showing the result of [$^3$H] HC3 binding to the membrane prepared from COS7 cells being introduced with CHT1 cDNA of the present invention or vector pcDNA 3.1 separately.
Figure 16:
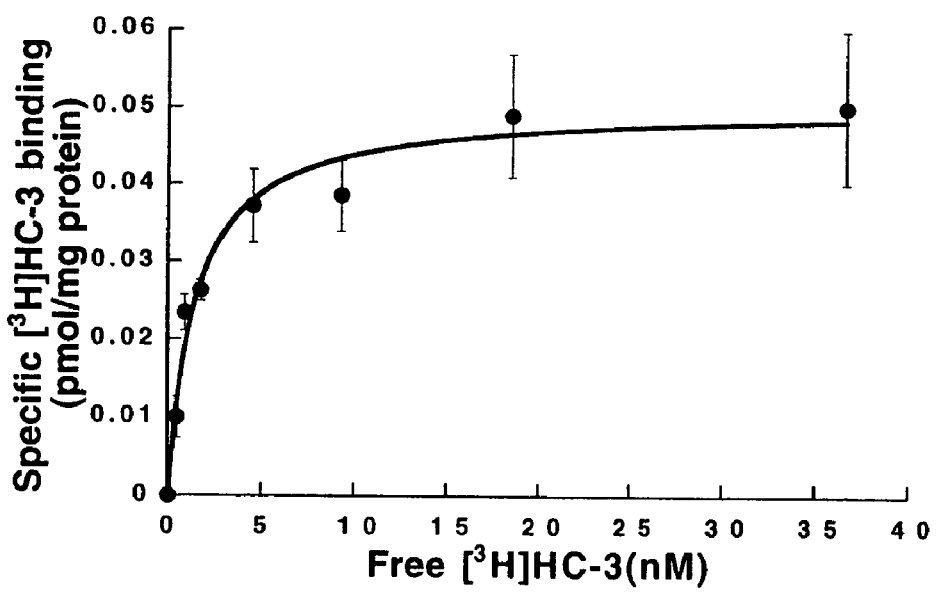
FIG. 16 is a view showing the result of saturation analysis of specific [$^3$H] HC3 binding to the membrane prepared from COS7 cells being introduced with CHT1 cDNA of the present invention or vector pcDNA 3.1 separately.
Figure 17:
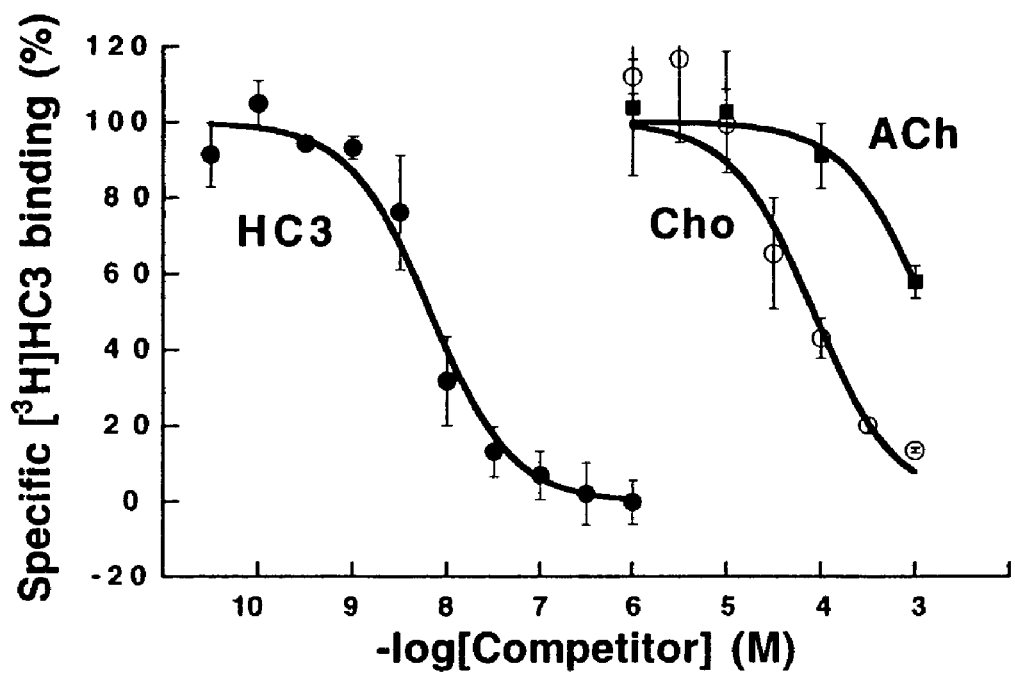
FIG. 17 is a view showing the result of displacement of specific [$^3$H] HC3 binding by HC3 of the present invention, choline (Cho), acetylcholine (ACh).

In addition, [$^3$H] HC3 binding activity of membranes prepared from COS7 cells introduced with CHT1 cDNA and a vector (control) respectively was examined. The result is shown in FIG. 15. As FIG. 15 indicates, $Na^+$-dependent [$^3$H] HC3 binding was observed in a membrane of a cell where CHT1 was expressed, but not in a control membrane. Subsequently, a saturation analysis was conducted for specific [$^3$H] HC3 binding. As shown in FIG. 16, equilibrium dissociation constant (Kd) was estimated to be 1.6±0.2 μM(n=3). This value was similar to that reported in brain synaptosomes (J. Neurochem. 60, 1191-1201, 1993, Life Sci. 35, 2335-2343, 1984, Brain Res. 348, 321-330, 1985). Further, displacement of specific [$^3$H] HC3 binding by HC3, choline (Cho) and acetylcholine (Ach) was examined. Acetylcholine was measured in the presence of 1 μM physostigmine. The result is shown in FIG. 17. FIG. 17 indicates that specific [$^3$H] HC3 binding was displaced when the concentration of choline was at least about 10 times lower than that of acetylcholine. These results show that CHT1 is a HC3 binding site as well as a high-affinity choline transporter.

The cDNA of human high-affinity choline transporter of the present invention, being represented by Seq. ID No.5, can be prepared, for example, as follows: data base search was conducted with the amino acid sequence of nematode (*C. elegans*) CHO-1 to find a sequence of specific human genome DNA fragment having significant homology (R-107P12, a clone of human genomic survey sequence; GenBank accession number: AQ316435); a gene-specific primers for PCR were designed based on a base sequence of said DNA fragment; 5'-RACE (rapid amplification of cDNA ends) and 3'-RACE were conducted using Marathon-Ready™ cDNA (Clontech) of human whole brain, together with an attached adapter primer; the obtained PCR product was cloned into a cloning vector for PCR, and a base sequence of inserted DNA was determined. In addition, an amino acid sequence expected from this DNA sequence is represented by Seq. ID No. 6. A protein having human high-affinity choline transporter activity represented by said Seq. ID No. 6 can be constructed by a usual method on the basis of DNA sequence information shown in Seq. ID No. 5.

The cDNA of mouse high-affinity choline transporter of the present invention, being represented by Seq. ID No.7, can be prepared, for example, as follows: data base search was conducted with the amino acid sequence of nematode (*C. elegans*) CHO-1 to find a sequence of specific human genome DNA fragment having significant homology (R-107P12, a clone of human genomic survey sequence; GenBank accession number: AQ316435); a gene-specific primer for PCR was designed based on a base sequence of said DNA fragment; 5'-RACE (rapid amplification of cDNA ends) and 3'-RACE were conducted using Marathon-Ready™ cDNA (Clontech) of mouse whole brain, together with an attached adapter primer; the obtained PCR product was cloned into a cloning vector for PCR, and a base sequence of inserted DNA was determined. In addition, an amino acid sequence expected from this DNA sequence is represented by Seq. ID No. 8. A protein having mouse high-affinity choline transporter activity represented by said Seq. ID No. 8 can be constructed by a usual method on the basis of DNA sequence information shown in Seq. ID No. 7.

Examples of a protein having high-affinity choline transporter activity of the present invention include a protein derived from natural materials and a recombinant protein. In addition to the ones represented by Seq. ID Nos. 2, 4, 6 and 8, which are specifically disclosed above, a protein comprising an amino acid sequence wherein one or a few amino acids are deficient, substituted or added in amino acid sequences represented by Seq. ID Nos. 2, 4, 6 and 8, and having high-affinity choline transporter activity is also included. These proteins can be prepared by known methods. Further, examples of a gene or DNA encoding a protein having high-affinity choline transporter activity of the present invention include, in addition to the ones represented by Seq. ID Nos. 1, 3, 5 and 7, which are specifically disclosed above, a gene or DNA which encodes a protein comprising an amino acid sequence wherein one or a few amino acids are deficient, substituted or added in amino acid sequences represented by Seq. ID Nos. 2, 4, 6 and 8, and having high-affinity choline transporter activity, and DNA which encodes a protein hybridizing with said gene or DNA under a stringent condition and having high-affinity choline transporter activity. These genes and DNAs can be prepared by known methods.

Cholinergic neurons play an extremely important role in learning and memory. The damage of these neurons correlates to severity of dementia. The rate-limiting step in acetylcholine synthesis is presumed to be the uptake of choline, and its activity is controlled by neural activity or various kinds of stimuli. In the brains of patients who suffer Alzheimer's disease, the hyperfunction of high-affinity choline uptake and of HC3 binding activity are observed (Trends Neurosci. 15, 117-122, 1992, Ann. NY Acad. Sci. 777, 197-204, 1996, J. Neurochem. 69, 2441-2451, 1997). Cloning of said gene or DNA encoding a protein having high-affinity choline transporter activity and said protein having high-affinity choline transporter activity is important for elucidating the molecular mechanism of the high-affinity choline transporter and for developing new therapies for Alzheimer's disease.

The fusion protein of the present invention means a substance constructed by binding a protein from a nematode, a rat, a human, a mouse, etc., which has high-affinity choline transporter activity, to a marker protein and/or a peptide tag. As the marker protein, any conventionally known marker protein can be used and the specific examples are alkaline phosphatase, Fc region of an antibody, HRP, and GFP. Conventionally known peptide tags, such as Myc tag, His tag, FLAG tag, GST tag, are exemplified as specific examples of the peptide tag of the present invention. Said fusion proteins can be constructed by a usual method, and are useful for the purification of a protein having high-affinity choline transporter activity utilizing the affinity between Ni-NTA and His tag, the detection of a protein having high-affinity choline transporter activity, the quantitation of an antibody to a protein having high-affinity choline transporter activity, and as a diagnostic marker for Alzheimer's disease, and an investigational reagent in the field concerned.

As an antibody that specifically combines with a protein having high-affinity choline transporter activity of the present invention, an immunospecific antibody such as a monoclonal antibody, a polyclonal antibody, a chimeric antibody, a single stranded antibody, a humanized antibody and the like are concretely exemplified. Though these antibodies can be constructed by a usual method with the above-mentioned protein having high-affinity choline transporter activity as an antigen, a monoclonal antibody is more preferable among them because of its specificity. Said antibody that specifically binds to a protein having high-affinity choline transporter activity, such as a monoclonal antibody or the like, is useful, for instance, for the diagnosis of Alzheimer's disease, and for elucidation of molecular mechanism of a high-affinity choline transporter.

An antibody to a protein having high-affinity choline transporter activity is developed by administering fragments containing the protein having high-affinity choline transporter activity or its epitope, or cells that express said protein on the surface of the membrane, to animals (preferably excluding human) with usual protocol. For instance, a monoclonal antibody can be prepared by an arbitrary method that brings antibodies developed by cultured materials of continuous cell line, such as hybridoma method (Nature 256,495-497, 1975), trioma method, human B-cell hybridoma method (Immunology Today 4, 72, 1983), and EBV-hybridoma method (MONOCLONAL ANTIBODIES AND CANCER THERAPY, pp. 77-96, Alan R. Liss, Inc., 1985).

In order to develop a single stranded antibody to the above-mentioned protein having high-affinity choline transporter activity of the present invention, the preparation method of single stranded antibodies (U.S. Pat. No. 4,946,778) can be applied. Further, in order to express a humanized antibody, it is possible to use transgenic mice, other mammalian animals or the like, and to isolate and identify the clones that express a protein having high-affinity choline transporter activity with the above-mentioned antibodies, and to purify the polypeptide by affinity chromatography. An antibody to a protein having high-affinity choline transporter activity could be used, in particular, for the diagnosis and the medical treatment of Alzheimer's disease, and the like.

This invention relates to a host cell which contains an expression system that can express said protein having high-affinity choline transporter activity. The gene that encodes a protein having high-affinity choline transporter activity can be introduced into a host cell by a number of methods described in many standard laboratory manuals such as by Davis et al. (BASIC METHODS IN MOLECULAR BIOLOGY, 1986), and by Sambrook et al. (MOLECULAR CLONING: A LABORATORY MANUAL, 2nd Ed., Cold Spring Harbor Laboratory Press, Cold Spring Harbor, N.Y., 1989). Examples of those methods include calcium phosphate transfection, DEAE-dextran-mediated transfection, transvection, microinjection, cationic lipid-mediated transfection, electroporation, transduction, scrape loading, ballistic introduction and infection. Examples of the host cells include bacterial procaryotic cells such as *Escherichia coli, Streptomyces, Bacillus subtilis, Streptococcus, Staphylococcus* and the like; fungous cells such as yeast, *Aspergillus* and the like; insect cells such as *drosophila* S2, spodptera Sf9 and the like; and animal or plant cells such as L cells, CHO cells, COS cells, HeLa cells, C127 cells, BALB/c3T3 cells (including mutant strains deficient in dihydrofolate reductase, thymidine kinase or the like), BHK21 cells, HEK293 cells, Bowes melanoma cells and the like.

As the expression system, any expression system that can express a protein having high-affinity choline transporter activity in a host cell will suffice. Examples of the expression system include expression systems derived from chromosome, episome and virus, for example, vectors derived from bacterial plasmid, yeast plasmid, papovavirus like SV40, vaccinia virus, adenovirus, chicken pox virus, pseudorabies virus, or retrovirus, vectors derived from bacteriophage, transposon, and the combination of these, for instance, vectors derived from genetic factors of plasmid and of bacteriophage such as cosmid or phagemid. These expression systems may contain a regulatory sequence that acts not only as a promoter but also as a controller of expressions.

A host cell that contains the above-mentioned expression system, cell membrane of said host cell, and a protein having high-affinity choline transporter activity which is obtainable by the cultivation of said host cell can be used in the screening method of the present invention as hereinafter described. For example, the method of F. Pietri-Rouxel et al. (Eur. J. Biochem., 247, 1174-1179, 1997) or the like can be used as the method to obtain cell membranes, and publicly known methods including ammonium sulfate or ethanol precipitation, acid extraction, anion or cation exchange chromatography, phosphocellulose chromatography, hydrophobic-interaction chromatography, affinity chromatography, hydroxyapatite chromatography, and lectin chromatography, preferably high-speed liquid chromatography can be used to pick up said protein having high-affinity choline transporter activity from cell cultured material and purify it. As columns used for affinity chromatography, in particular, there are columns to which a protein antibody having anti-high-affinity choline transporter activity is bound, or in case that a normal peptide tag is added to said high-affinity choline transporter, there are columns to which materials having affinity to the peptide tag are bound. Proteins having high-affinity choline transporter activity can be obtained by using these columns.

In the present invention, said non-human animal whose function of a gene encoding a protein having high-affinity choline transporter activity is deficient on its chromosome means a non-human animal wherein a part or a whole of a gene encoding a protein having high-affinity choline transporter activity on chromosome is inactivated by gene mutation such as disruption, deficiency, substitution, etc. and function of expressing a protein having high-affinity choline transporter activity is lost. In addition, a non-human animal that overexpresses function of a gene that encodes a protein having high-affinity choline transporter activity on its chromosome means a non-human animal that produces larger amount of a protein having high-affinity choline transporter activity than a wild-type non-human animal does. Though specific examples of a non-human animal of the present invention include rodents, such as mice, rats and the like, a non-human animal of the present invention is not limited to these animals.

Homozygous non-human animals generated according to Mendelian ratio include a deficient type or an overexpression type for a protein having high-affinity choline transporter activity, and their littermate wild-type, and it is possible to carry out precise comparative experiments in individual level by using the deficient types, the overexpression types and the littermate wild-types of these homozygous non-human animals at the same time. Therefore, it is preferable to use animals of the same species, more preferably the littermates, as the wild-type non-human animals, in other words, the non-human animals being deficient in or overexpressing the function of a gene that encodes a protein having high-affinity choline transporter activity on their chromosome together in, for example, the screening hereinafter described in the present invention. The generating method of the non-human animals being deficient or overexpressing the function of a gene that encodes a protein having high-affinity choline transporter activity on their chromosome will be explained below, with an example of knockout mice and transgenic mice of a protein having high-affinity choline transporter activity.

For example, a mouse being deficient in the function of a gene that encodes a protein having high-affinity choline transporter activity on its chromosome, in other words, a knockout mouse of a protein having high-affinity choline transporter activity on its chromosome can be constructed as follows. A gene that encodes a protein having high-affinity choline transporter activity is screened by using a gene fragment obtained from mouse gene library by a method like PCR. The screened gene that encodes a protein having high-affinity choline transporter activity is subcloned with a viral vector or the like, and specified by DNA sequencing. A target vector is constructed by substituting a whole or a part of a gene of this clone that encodes a protein having high-affinity choline transporter activity with pMC1 neo gene cassette or the like, and by introducing a diphtheria toxin A fragment (DT-A) gene, a herpes simplex virus thymidine kinase (HSV-tk) gene or other such genes into 3'-terminal side.

This constructed target vector is linearized and introduced into ES cells by electroporation or the like to induce homologous recombination. The ES cells wherein homologous recombination is induced by an antibiotic such as G418, ganciclovir (GANC) or the like are selected from the homologous recombinants. It is preferable to confirm whether the selected ES cells are the recombinants of the object by Southern blot or the like. A chimeric mouse is constructed by microinjecting a clone of the confirmed ES cells into a blastocyst of a mouse and then transplanting the blastocyst into a recipient mouse. A heterozygous mouse can be obtained by interclossing the chimeric mouse with a wild-type mouse, and a knockout mouse of a protein having high-affinity choline transporter activity of the present invention can be constructed by interclossing the heterozygous mice. It is possible to confirm whether a knockout mouse of a protein having high-affinity choline transporter activity is constructed, for example, by isolating RNA from the mouse obtained by said method and examining it by Northern blot analysis or the like, or by examining the expression of the mouse by Western blot analysis or the like.

The transgenic mice of a protein having high-affinity choline transporter activity can be generated in following procedures. A transgene is constructed by fusing chicken β-actin, mouse neurofilament, SV40 or other such promoters, and rabbit β-globin, SV40 or other such poly A or introns with cDNA that encodes a protein having high-affinity choline transporter activity. The transgene is microinjected into the pronucleus of a fertilized egg of a mouse, and the obtained egg cell is cultured, then transplanted to the oviduct of a recipient mouse. After rearing up the recipient animal, baby mice that have the above-mentioned cDNA are selected from the mice born from the recipient animal. Thus transgenic mice can be generated. The baby mouse that has cDNA can be selected by extracting crude DNA from a tail or the like of a mouse, then carrying out methods like dot hybridization using the introduced gene that encodes a protein having high-affinity choline transporter activity as a probe, PCR method using a specific primer, and the like.

In addition, cells being useful for gene therapy of Alzheimer's disease and the like can be prepared by using a whole or a part of a gene or DNA that encodes a protein having high-affinity choline transporter activity of the present invention. As an example of a method for preparing these cells of the present invention, a method wherein a whole or a part of said gene or DNA of the present invention is introduced into a cell being deficient in the function of a gene that encodes a protein having high-affinity choline transporter activity on its chromosome by transfection or the like to obtain a cell having high-affinity choline transporter activity is exemplified. As the cell having high-affinity choline transporter activity, in particular, it is preferable to use a cell wherein said gene or DNA is integrated into a chromosome and high-affinity choline transporter activity is exhibited stably.

By using the above-mentioned gene or DNA that encodes a protein having high-affinity choline transporter activity, a protein having high-affinity choline transporter activity, a fusion protein created by combining a protein having high-affinity choline transporter activity and a marker protein and/or a peptide tag, an antibody to a protein having high-affinity choline transporter activity, a host cell which contains an expression system that can express a protein having high-affinity choline transporter activity, a cell having high-affinity choline transporter activity, or the like, it becomes possible to screen a pharmaceutical material useful for the treatment of symptoms as in Alzheimer's disease or the like, in other words, a material that promotes or suppresses the activity or the expression of a high-affinity choline transporter.

Examples of the screening method of the present invention are: a method wherein the high-affinity choline transporter activity of the above-mentioned protein having high-affinity choline transporter activity of the present invention is measured/evaluated in the presence of a subject material; a method wherein a cell membrane or a cell which expresses a protein having high-affinity choline transporter activity of the present invention is cultivated in vitro in the presence of a subject material, and the activity and/or the expression amount of a protein having high-affinity choline transporter activity in the cell is measured/evaluated; and a method wherein a subject material is administered to said non-human animal whose function of a gene encoding a protein having high-affinity choline transporter activity is deficient or overexpresses on its chromosome and/or a wild-type non-human animal and then the activity and/or the expression amount of a protein having high-affinity choline transporter activity of the present invention is measured/evaluated. As said cell membrane or said cell, a cell such as a primary cultured cell obtained from said non-human animal whose function of a gene encoding a protein having high-affinity choline transporter activity is deficient or overexpresses on its chromosome or a wild-type non-human animal etc., a host cell containing an expression system which can express a protein having high-affinity choline transporter activity of the present invention, a cell having high-affinity choline transporter activity of the present invention, and cell membranes of these cells can be specifically exemplified.

The screening methods with said subject material and said protein having high-affinity choline transporter activity are now specifically explained together with examples, but the screening methods of the present invention are not limited to these examples. Cells expressing a protein having high-affinity choline transporter activity are cultured in the presence of a subject material, and the increase or the decrease of a protein having high-affinity choline transporter activity expressed on the cell surface after a certain period of cultivation can be immunochemically detected by ELISA or other such method with an antibody that specifically combines to a protein having high-affinity choline transporter activity of the present invention, or can be evaluated by using suppression or promotion of mRNA expression as an index. The mRNA can be detected by methods such as DNA chip, Northern hybridization or the like. Moreover, with a cell to which a gene wherein luciferase or other such reporter genes is linked to downstream of promoter of a gene that encodes high-affinity choline transporter is introduced, the suppression or the promotion of the expression of a gene that encodes a protein having high-affinity choline transporter activity induced by a subject material can be detected by using the activity of said reporter gene as an index.

The present invention further relates a medical constituent being used for medical treatment for a patient who needs promotion of the activity or the expression of a protein having high-affinity choline transporter, or a medical constituent being used for medical treatment for a patient who needs suppression of the activity or the expression of a protein having high-affinity choline transporter, wherein the material contains a protein having high-affinity choline transporter activity, a material which promotes the activity or the expression of a protein having high-affinity choline transporter activity, or a material which suppresses activity or expression of a protein having high-affinity choline transporter activity as an active component. As a protein having high-affinity choline transporter activity is involved in many biological functions including many pathological ones, it is expected that a compound that can stimulate a protein having high-affinity choline transporter activity and a compound being able to inhibit the function of said protein can be used as pharmaceuticals.

As the material which promotes or suppresses the activity or the expression of a protein having high-affinity choline transporter activity, any material can be used as long as it binds to a protein having high-affinity choline transporter activity, or works on a signal transmitting molecule on upstream, and then promotes the activity or the expression of a protein having high-affinity choline transporter activity or inhibits/antagonizes the activity or the expression of the protein by itself. Specific examples include an antibody, a ligand of a protein having high-affinity choline transporter activity, a fragment of said protein, and an oligonucleotide encoding said fragment, and these materials can be used as pharmaceuticals for treatment, prevention or the like of symptoms observed in the case of Alzheimer's disease or other such diseases, but use of them is not limited to the above examples.

The present invention also relates to a diagnostic method for diseases relating to the activity or the expression of a protein having high-affinity choline transporter activity comprising a comparison of a DNA sequence encoding a protein having high-affinity choline transporter activity in a sample with a DNA sequence encoding a protein having high-affinity choline transporter activity of the present invention. The mutant type of DNA which encodes a protein having high-affinity choline transporter activity can be detected by finding gene-mutated individuals in DNA level, and this is useful for diagnosis of diseases caused by underexpression, overexpression or mutant expression of a protein having high-affinity choline transporter activity. Specific examples of a sample of said detection include cells of trial subjects, for example, genomic DNA, RNA or cDNA obtained from biopsy of blood, urine, saliva, tissue or the like, however said sample is not limited to these examples. It is also possible to use said sample being amplified by PCR or other such methods. Deficiency and insertion mutation of base sequences can be detected by the size change of the amplified product observed in comparison with normal genotype, and point mutation can be identified by hybridizing amplified DNA with a labeled gene that encodes a protein having high-affinity choline transporter activity. Thus, diagnosis or judgement of symptoms observed in the case of Alzheimer's disease or other such diseases can be made by detecting the mutation of a gene that encodes a protein having high-affinity choline transporter activity.

The present invention further relates to a diagnostic probe for diseases showing symptoms similar to those of Alzheimer's disease or the like comprising a whole or a part of an antisense chain of DNA or RNA encoding a protein having high-affinity choline transporter activity, and a diagnostic drug for diseases showing symptoms similar to those of Alzheimer's disease containing the diagnostic probe and/or an antibody which specifically binds to a protein having high-affinity choline transporter activity of the present invention. Said diagnostic probe is not limited in particular, as long as it comprises a whole or a part of an antisense chain of DNA (cDNA) or RNA (cRNA) encoding a protein having high-affinity choline transporter activity and being long enough to be a probe (at least 20 bases). In order to make a diagnostic drug for symptoms similar to those of Alzheimer's disease containing said probe and/or an antibody which specifically binds to a protein having high-affinity choline transporter activity of the present invention as active components, it is preferable to dissolve said probe into an appropriate buffer or sterilizing water for preventing said probe from decomposition. Further, it is also possible to diagnose diseases showing symptoms similar to those of Alzheimer's disease by methods using these diagnostic drugs, such as immunostaining (Dev. Biol. 170, 207-222, 1995, J. Neurobiol. 29, 1-17, 1996), in situ hybridization (J. Neurobiol. 29, 1-17, 1996), in situ PCR or the like.

Experimental methods or the like of the above-mentioned various experiments will now be explained in more detail below.

(Cloning of High-Affinity Choline Transporter cDNA)

The candidate cDNA of nematode high-affinity choline transporter was isolated from poly (A)+RNA of nematode mixture from various stages in the development by reverse transcription PCR and 3' RACE. Marathon™ cDNA Amplification Kit (Clontech) was used according to its protocol. A primer for sense direction of PCR was designed at a provisional translation initiating point of a predicted gene based on a DNA base sequence obtained from *C. elegans* genomic project. The amplified PCR product was subcloned into Nco I (smoothing) site and Not I site of a modified pSPUTK vector (Stratagene), and the base sequence of inserted DNA was determined. CHT1 cDNA of rat was isolated from rat spinal cord cDNA library by using GeneTrapper cDNA Positive Selection System (GIBCO Bio-Rad Laboratory: GIBCO BRL) according to its protocol. The primer used was designed from the base sequence of a cDNA fragment obtained by degenerated PCR. The obtained cDNA clones were analyzed. Among them, positive clones were selected and subcloned into pSPUTK vector and pcDNA3.1+ vector (Invitrogen Corporation).

(Expression in Oocytes of *Xenopus*)

In the presence of cap analog, cRNA was synthesized in vitro with SP6 or T7 RNA polymerase. 20 to 30 ng capped RNA was microinjected into oocytes (stage V to VI) of *Xenopus*. The uptake was measured in basically same manner as described previously (Nature 360,467-471, 1992). Two or three days after the injection of RNA, choline uptake was conducted for 30 to 60 min. with oocytes (6 to 8) in 0.75 ml standard solution (0.01 to 1 μM [$^3$H]-choline, 100 mM NaCl, 2 mM KCl, 1 mM $MgCl_2$, 1 mM $CaCl_2$, 10 mM HEPES, 5 mM Tris: pH 7.4). The oocytes completing uptake were solubilized with 10% SDS, and the amount of [$^3$H] was measured by a liquid scintillation counter.

(GFP Expression Construct)

The transcriptional fusion construct of cho-1::gfp was constructed by PCR in same manner as described previously (Gene 212, 127-135, 1998). A gene that encodes a green fluorescent protein (GFP) located on downstream of a nuclear localization signal sequence (NLS) was inserted into a position 3 residues downstream of cho-1 translation initiating point so that the reading frame was fitted. NLS and gfp gene were amplified from pPD104.53 vector. In order to prepare 5.1 kb upstream region of cho-1 translation initiating point, a PCR primer being designed to encompass the first 3 amino acid residues of cho-1 was used. By the same method as previously described (EMBO J. 10, 3959-3970, 1991), rol-6 (su1006) marker and generated DNA were injected into gonads of a nematode simultaneously.

(Northern Blot Analysis)

6 μg poly(A)+RNA prepared from various tissues of rats was separated by formaldehyde-agarose electrophoresis, and transferred to a nylon membrane, then hybridized with CHT1 cDNA fragment being labeled with [$^{32}$P] by random prime method in hybridization solution (solution containing the final concentration of 50% formamido, 5×SSPE, 5×Denhardt's solution, 0.5% SDS, 100 μg/ml salmon sperm DNA) at 42° C. for 16 hours. The nylon membrane was washed under final condition (0.1×SSPE, 0.1% SDS: 65° C.), and then autoradiography was conducted for 7 days together with an enhancing screen.

(In Situ Hybridization)

The transcript of an antisense labeled with digoxigenin was synthesized in vitro. Alkaline hydrolysis was repeated for the transcripts until their mean length was prepared to be 200 to 400 b. Cryostat sections of fresh frozen tissue (10 to 20 μm) were used. Hybridization was conducted with labeled cRNA probe (about 1 μg/ml) dissolved in 1×Denhardt's solution [solution containing the final concentration of 50 mM Tris-HCl (pH 8.0), 2.5 mM EDTA, 0.3 M NaCl, 50% formamido, 10% dextran sulphate, 1 mg/ml E. coli tRNA] at 45° C. for 20 hours. Then the sections were washed twice in 2×SSC/50% formamido and once in 1×SSC/50% formamido, at 45° C. respectively. The hybridized probe was visualized by using anti-digoxigenin Fab fragment (Boehringer-Mannheim) and NBT/BCIP substrate. The sections were brought into reaction in substrate solution for 24 to 48 hours.

(Binding Assay)

[$^3$H] hemicholinium-3 (HC3; 128Ci/mmol) was obtained from NEN Life Science Products. Either pcDNA3.1-CHT1 or pcDNA3.1 was transiently expressed in COS7 cells respectively. TransFast Reagent (Promega) was introduced and used according to the protocol. Membranes were prepared by following steps: homogenizing cells in 0.32 M sucrose; centrifuging the cells for 1 hour at 200,000 g; and suspending the precipitate. Binding assay was conducted in basically same manner as described previously. Specific binding amount was calculated by subtracting non-specific binding amount determined in the presence of 10 μM HC3 from the whole binding amount. The Kd value was figured out by analyzing specific [$^3$H] HC3 binding amount from data of saturation binding assay with nonlinear approximation.

INDUSTRIAL APPLICABILITY

The present invention makes it possible to provide a protein having high-affinity choline transporter activity, which is physiologically important, and gene DNA encoding said protein. In addition, by using the said protein and gene DNA, it becomes possible to screen materials being useful for prevention or treatment of Alzheimer's disease, and to prepare cells being useful for gene therapy.

What is claimed is:

1. An isolated nucleic acid which encodes a protein comprising an amino acid sequence represented by Seq. ID No. 6.

2. An isolated protein comprising an amino acid sequence represented by Seq. ID No. 6.

3. A fusion protein wherein the protein according to claim 2 and a marker protein and/or peptide tag are bound together.

4. An isolated host cell comprising an expression system capable of expressing the protein according to claim 2.

* * * * *

SEQUENCE LISTING

```
<160> NUMBER OF SEQ ID NOS: 8

<210> SEQ ID NO 1
<211> LENGTH: 1731
<212> TYPE: DNA
<213> ORGANISM: Caenorhabditis elegans
<220> FEATURE:
<221> NAME/KEY: CDS
<222> LOCATION: (1)..(1731)

<400> SEQUENCE: 1 atg gcc gac tta ttg ggt atc gtg gcc att gtg ttc ttc tac gtg ctc       48
Met Ala Asp Leu Leu Gly Ile Val Ala Ile Val Phe Phe Tyr Val Leu
 1               5                  10                  15 att ctt gtc gtt gga ata tgg gcg ggt aga aaa tcg aaa agt tca aaa       96
Ile Leu Val Val Gly Ile Trp Ala Gly Arg Lys Ser Lys Ser Ser Lys
            20                  25                  30 gag ctt gaa tca gaa gcc ggc gcg gcg acg gaa gag gtg atg tta gct      144
Glu Leu Glu Ser Glu Ala Gly Ala Ala Thr Glu Glu Val Met Leu Ala
        35                  40                  45 ggg aga aac atc gga act ctt gtc gga att ttc aca atg act gcc acg      192
Gly Arg Asn Ile Gly Thr Leu Val Gly Ile Phe Thr Met Thr Ala Thr
    50                  55                  60 tgg gtt ggc ggt gct tat atc aat gga acc gcc gag gct ctg tat aat      240
Trp Val Gly Gly Ala Tyr Ile Asn Gly Thr Ala Glu Ala Leu Tyr Asn
65                  70                  75                  80 gga ggt ctc ctt gga tgt cag gct cca gtt gga tat gca att tcc ctt      288
```

```
                                                                              -continued Gly Gly Leu Leu Gly Cys Gln Ala Pro Val Gly Tyr Ala Ile Ser Leu
                 85                  90                  95 gtt atg gga gga cta ctt ttc gca aag aaa atg cga gaa gaa gga tat          336
Val Met Gly Gly Leu Leu Phe Ala Lys Lys Met Arg Glu Glu Gly Tyr
            100                 105                 110 att aca atg ctc gat cct ttt cag cac aaa tat ggc caa cga atc ggt          384
Ile Thr Met Leu Asp Pro Phe Gln His Lys Tyr Gly Gln Arg Ile Gly
            115                 120                 125 ggc ttg atg tat gtt cca gca ctt ctt ggt gaa aca ttc tgg aca gca          432
Gly Leu Met Tyr Val Pro Ala Leu Leu Gly Glu Thr Phe Trp Thr Ala
    130                 135                 140 gcc att ctt tcg gca ctt ggt gca aca ctg tcg gta att ctt gga atc          480
Ala Ile Leu Ser Ala Leu Gly Ala Thr Leu Ser Val Ile Leu Gly Ile
145                 150                 155                 160 gac atg aat gca tca gtg acc ctg tcg gcc tgt att gcc gta ttc tac          528
Asp Met Asn Ala Ser Val Thr Leu Ser Ala Cys Ile Ala Val Phe Tyr
                165                 170                 175 aca ttc acc ggt gga tac tat gca gtc gcg tac act gac gtc gtt caa          576
Thr Phe Thr Gly Gly Tyr Tyr Ala Val Ala Tyr Thr Asp Val Val Gln
            180                 185                 190 cta ttt tgc att ttc gtc ggt ttg tgg gtt tgc gtg ccg gcg gct atg          624
Leu Phe Cys Ile Phe Val Gly Leu Trp Val Cys Val Pro Ala Ala Met
        195                 200                 205 gtg cat gat ggt gcg aag gat att tcc agg aat gca ggc gac tgg att          672
Val His Asp Gly Ala Lys Asp Ile Ser Arg Asn Ala Gly Asp Trp Ile
    210                 215                 220 gga gag att gga gga ttc aaa gaa aca tct ctc tgg att gat tgc atg          720
Gly Glu Ile Gly Gly Phe Lys Glu Thr Ser Leu Trp Ile Asp Cys Met
225                 230                 235                 240 ctt ctc ctt gtc ttt gga gga att cca tgg caa gtg tac ttc caa aga          768
Leu Leu Leu Val Phe Gly Gly Ile Pro Trp Gln Val Tyr Phe Gln Arg
                245                 250                 255 gtt ctc tcc tca aaa act gct cat gga gca cag acg ttg tcg ttt gtg          816
Val Leu Ser Ser Lys Thr Ala His Gly Ala Gln Thr Leu Ser Phe Val
            260                 265                 270 gcg ggc gtc gga tgc att ctc atg gcg att cca cca gcg ttg atc ggt          864
Ala Gly Val Gly Cys Ile Leu Met Ala Ile Pro Pro Ala Leu Ile Gly
        275                 280                 285 gca att gcc agg aac aca gac tgg aga atg act gat tat tcc cca tgg          912
Ala Ile Ala Arg Asn Thr Asp Trp Arg Met Thr Asp Tyr Ser Pro Trp
    290                 295                 300 aac aat gga act aag gtc gaa tcg att cca ccg gat aag aga aac atg          960
Asn Asn Gly Thr Lys Val Glu Ser Ile Pro Pro Asp Lys Arg Asn Met
305                 310                 315                 320 gtg gtc ccg ttg gta ttc cag tat ctt acg cca aga tgg gtc gcc ttt         1008
Val Val Pro Leu Val Phe Gln Tyr Leu Thr Pro Arg Trp Val Ala Phe
                325                 330                 335 att gga ctc ggc gca gtg tcg gct gct gta atg tca tct gca gat tca         1056
Ile Gly Leu Gly Ala Val Ser Ala Ala Val Met Ser Ser Ala Asp Ser
            340                 345                 350 tct gta cta tca gca gca tca atg ttt gct cac aac atc tgg aag ctc         1104
Ser Val Leu Ser Ala Ala Ser Met Phe Ala His Asn Ile Trp Lys Leu
        355                 360                 365 aca att cgc cct cac gcg tct gaa aaa gaa gtg ata att gtg atg aga         1152
Thr Ile Arg Pro His Ala Ser Glu Lys Glu Val Ile Ile Val Met Arg
    370                 375                 380 ata gcc atc atc tgt gtt ggt atc atg gca acc atc atg gca ctt acc         1200
Ile Ala Ile Ile Cys Val Gly Ile Met Ala Thr Ile Met Ala Leu Thr
385                 390                 395                 400
```

-continued

```
att caa tcc atc tat ggg ctt tgg tat ctt tgt gca gat ttg gtc tac      1248
Ile Gln Ser Ile Tyr Gly Leu Trp Tyr Leu Cys Ala Asp Leu Val Tyr
            405                 410                 415 gtc ata ctc ttc cct caa cta tta tgt gtt gta tat atg cca cgt agc      1296
Val Ile Leu Phe Pro Gln Leu Leu Cys Val Val Tyr Met Pro Arg Ser
        420                 425                 430 aat acg tat ggc tca ttg gct ggc tat gca gtc ggt ctt gtg ctc cgt      1344
Asn Thr Tyr Gly Ser Leu Ala Gly Tyr Ala Val Gly Leu Val Leu Arg
    435                 440                 445 ttg att gga ggc gag cca ctt gta tcg ctg cca gcg ttc ttc cat tat      1392
Leu Ile Gly Gly Glu Pro Leu Val Ser Leu Pro Ala Phe Phe His Tyr
450                 455                 460 cca atg tat acg gat ggg gta cag tat ttc cca ttc agg aca act gct      1440
Pro Met Tyr Thr Asp Gly Val Gln Tyr Phe Pro Phe Arg Thr Thr Ala
465                 470                 475                 480 atg tta tct tca atg gct act atc tac att gta tca ata caa tcg gag      1488
Met Leu Ser Ser Met Ala Thr Ile Tyr Ile Val Ser Ile Gln Ser Glu
                485                 490                 495 aag ctg ttc aaa tcg gga cgt ttg tct ccg gag tgg gac gta atg ggt      1536
Lys Leu Phe Lys Ser Gly Arg Leu Ser Pro Glu Trp Asp Val Met Gly
            500                 505                 510 tgt gta gtg aat att ccg ata gat cat gta ccc ctt ccg tca gat gta      1584
Cys Val Val Asn Ile Pro Ile Asp His Val Pro Leu Pro Ser Asp Val
        515                 520                 525 tcg ttt gct gtt agt agt gag acc ttg aat atg aag gct cca aac gga      1632
Ser Phe Ala Val Ser Ser Glu Thr Leu Asn Met Lys Ala Pro Asn Gly
    530                 535                 540 aca ccg gct cca gta cat ccg aac caa cag ccg tct gat gaa aat aca      1680
Thr Pro Ala Pro Val His Pro Asn Gln Gln Pro Ser Asp Glu Asn Thr
545                 550                 555                 560 tta tta cat cca tat tcg gac caa agt tat tat tcc aca aat agc aat      1728
Leu Leu His Pro Tyr Ser Asp Gln Ser Tyr Tyr Ser Thr Asn Ser Asn
                565                 570                 575 taa                                                                  1731

<210> SEQ ID NO 2
<211> LENGTH: 576
<212> TYPE: PRT
<213> ORGANISM: Caenorhabditis elegans

<400> SEQUENCE: 2

Met Ala Asp Leu Leu Gly Ile Val Ala Ile Val Phe Phe Tyr Val Leu
 1               5                  10                  15

Ile Leu Val Val Gly Ile Trp Ala Gly Arg Lys Ser Lys Ser Ser Lys
             20                  25                  30

Glu Leu Glu Ser Glu Ala Gly Ala Ala Thr Glu Glu Val Met Leu Ala
         35                  40                  45

Gly Arg Asn Ile Gly Thr Leu Val Gly Ile Phe Thr Met Thr Ala Thr
     50                  55                  60

Trp Val Gly Gly Ala Tyr Ile Asn Gly Thr Ala Glu Ala Leu Tyr Asn
 65                  70                  75                  80

Gly Gly Leu Leu Gly Cys Gln Ala Pro Val Gly Tyr Ala Ile Ser Leu
                 85                  90                  95

Val Met Gly Gly Leu Leu Phe Ala Lys Lys Met Arg Glu Glu Gly Tyr
            100                 105                 110

Ile Thr Met Leu Asp Pro Phe Gln His Lys Tyr Gly Gln Arg Ile Gly
        115                 120                 125

Gly Leu Met Tyr Val Pro Ala Leu Leu Gly Glu Thr Phe Trp Thr Ala
```

```
            130                 135                 140
Ala Ile Leu Ser Ala Leu Gly Ala Thr Leu Ser Val Ile Leu Gly Ile
145                 150                 155                 160

Asp Met Asn Ala Ser Val Thr Leu Ser Ala Cys Ile Ala Val Phe Tyr
                165                 170                 175

Thr Phe Thr Gly Gly Tyr Tyr Ala Val Ala Tyr Thr Asp Val Val Gln
                180                 185                 190

Leu Phe Cys Ile Phe Val Gly Leu Trp Val Cys Val Pro Ala Ala Met
                195                 200                 205

Val His Asp Gly Ala Lys Asp Ile Ser Arg Asn Ala Gly Asp Trp Ile
210                 215                 220

Gly Glu Ile Gly Gly Phe Lys Glu Thr Ser Leu Trp Ile Asp Cys Met
225                 230                 235                 240

Leu Leu Leu Val Phe Gly Gly Ile Pro Trp Gln Val Tyr Phe Gln Arg
                245                 250                 255

Val Leu Ser Ser Lys Thr Ala His Gly Ala Gln Thr Leu Ser Phe Val
                260                 265                 270

Ala Gly Val Gly Cys Ile Leu Met Ala Ile Pro Pro Ala Leu Ile Gly
                275                 280                 285

Ala Ile Ala Arg Asn Thr Asp Trp Arg Met Thr Asp Tyr Ser Pro Trp
290                 295                 300

Asn Asn Gly Thr Lys Val Glu Ser Ile Pro Pro Asp Lys Arg Asn Met
305                 310                 315                 320

Val Val Pro Leu Val Phe Gln Tyr Leu Thr Pro Arg Trp Val Ala Phe
                325                 330                 335

Ile Gly Leu Gly Ala Val Ser Ala Ala Val Met Ser Ser Ala Asp Ser
                340                 345                 350

Ser Val Leu Ser Ala Ala Ser Met Phe Ala His Asn Ile Trp Lys Leu
                355                 360                 365

Thr Ile Arg Pro His Ala Ser Glu Lys Glu Val Ile Ile Val Met Arg
370                 375                 380

Ile Ala Ile Ile Cys Val Gly Ile Met Ala Thr Ile Met Ala Leu Thr
385                 390                 395                 400

Ile Gln Ser Ile Tyr Gly Leu Trp Tyr Leu Cys Ala Asp Leu Val Tyr
                405                 410                 415

Val Ile Leu Phe Pro Gln Leu Leu Cys Val Val Tyr Met Pro Arg Ser
                420                 425                 430

Asn Thr Tyr Gly Ser Leu Ala Gly Tyr Ala Val Gly Leu Val Leu Arg
                435                 440                 445

Leu Ile Gly Gly Glu Pro Leu Val Ser Leu Pro Ala Phe Phe His Tyr
450                 455                 460

Pro Met Tyr Thr Asp Gly Val Gln Tyr Phe Pro Phe Arg Thr Thr Ala
465                 470                 475                 480

Met Leu Ser Ser Met Ala Thr Ile Tyr Ile Val Ser Ile Gln Ser Glu
                485                 490                 495

Lys Leu Phe Lys Ser Gly Arg Leu Ser Pro Glu Trp Asp Val Met Gly
                500                 505                 510

Cys Val Val Asn Ile Pro Ile Asp His Val Pro Leu Pro Ser Asp Val
                515                 520                 525

Ser Phe Ala Val Ser Ser Glu Thr Leu Asn Met Lys Ala Pro Asn Gly
                530                 535                 540

Thr Pro Ala Pro Val His Pro Asn Gln Gln Pro Ser Asp Glu Asn Thr
545                 550                 555                 560
```

```
Leu Leu His Pro Tyr Ser Asp Gln Ser Tyr Tyr Ser Thr Asn Ser Asn
            565                 570                 575

<210> SEQ ID NO 3
<211> LENGTH: 1743
<212> TYPE: DNA
<213> ORGANISM: Rattus norvegicus
<220> FEATURE:
<221> NAME/KEY: CDS
<222> LOCATION: (1)..(1743)

<400> SEQUENCE: 3 atg cct ttc cat gta gaa gga cta gta gcg att atc ctg ttc tac ctt      48
Met Pro Phe His Val Glu Gly Leu Val Ala Ile Ile Leu Phe Tyr Leu
 1               5                  10                  15 ctt ata ttt ctg gtt gga ata tgg gct gca tgg aaa acc aaa aac agc      96
Leu Ile Phe Leu Val Gly Ile Trp Ala Ala Trp Lys Thr Lys Asn Ser
             20                  25                  30 ggt aat gca gaa gaa cgc agc gaa gcc atc ata gtt ggg ggc cga gac     144
Gly Asn Ala Glu Glu Arg Ser Glu Ala Ile Ile Val Gly Gly Arg Asp
         35                  40                  45 att ggt ttg ttg gtt ggt ggt ttt acc atg aca gcc acc tgg gtt gga     192
Ile Gly Leu Leu Val Gly Gly Phe Thr Met Thr Ala Thr Trp Val Gly
 50                  55                  60 gga ggt tac atc aac ggg aca gct gaa gca gtt tat ggg cca ggt tgt     240
Gly Gly Tyr Ile Asn Gly Thr Ala Glu Ala Val Tyr Gly Pro Gly Cys
 65                  70                  75                  80 ggt cta gct tgg gct cag gca ccc att gga tat tct ctg agt ctg att     288
Gly Leu Ala Trp Ala Gln Ala Pro Ile Gly Tyr Ser Leu Ser Leu Ile
                 85                  90                  95 tta ggt ggc ctg ttt ttt gca aaa cct atg cgt tcc aag gga tat gtg     336
Leu Gly Gly Leu Phe Phe Ala Lys Pro Met Arg Ser Lys Gly Tyr Val
            100                 105                 110 act atg tta gac ccg ttt caa cag atc tat gga aag cgc atg ggt ggg     384
Thr Met Leu Asp Pro Phe Gln Gln Ile Tyr Gly Lys Arg Met Gly Gly
        115                 120                 125 ctg ctg ttc atc cct gca ctg atg gga gag atg ttc tgg gct gca gca     432
Leu Leu Phe Ile Pro Ala Leu Met Gly Glu Met Phe Trp Ala Ala Ala
    130                 135                 140 att ttc tct gca tta ggg gct acc atc agc gta atc att gat gtg gat     480
Ile Phe Ser Ala Leu Gly Ala Thr Ile Ser Val Ile Ile Asp Val Asp
145                 150                 155                 160 gtg aac ata tcg gtc att gtc tcc gca ctc att gcc att ctt tat acc     528
Val Asn Ile Ser Val Ile Val Ser Ala Leu Ile Ala Ile Leu Tyr Thr
                165                 170                 175 ctc gtg gga ggg ctc tac tct gtg gca tat act gat gtt gta cag cta     576
Leu Val Gly Gly Leu Tyr Ser Val Ala Tyr Thr Asp Val Val Gln Leu
            180                 185                 190 ttc tgc att ttt ata gga ttg tgg atc agt gtc cca ttt gcc ctg tca     624
Phe Cys Ile Phe Ile Gly Leu Trp Ile Ser Val Pro Phe Ala Leu Ser
        195                 200                 205 cat cct gca gtc acc gac att gga ttc act gct gtg cat gct aaa tac     672
His Pro Ala Val Thr Asp Ile Gly Phe Thr Ala Val His Ala Lys Tyr
    210                 215                 220 cag agt ccc tgg ctg gga acc att gaa tca gtt gaa gtc tac acc tgg     720
Gln Ser Pro Trp Leu Gly Thr Ile Glu Ser Val Glu Val Tyr Thr Trp
225                 230                 235                 240 ctt gat aat ttt ctg ttg ttg atg ctg ggt gga ata cca tgg caa gcc     768
Leu Asp Asn Phe Leu Leu Leu Met Leu Gly Gly Ile Pro Trp Gln Ala
                245                 250                 255
```

```
tac ttc cag agg gtc ctc tct tca tcg tca gcg acc tat gct cag gtg      816
Tyr Phe Gln Arg Val Leu Ser Ser Ser Ala Thr Tyr Ala Gln Val
            260                 265                 270 ctg tcc ttc ctg gca gct ttt ggg tgc ctg gtg atg gct cta cca gcc      864
Leu Ser Phe Leu Ala Ala Phe Gly Cys Leu Val Met Ala Leu Pro Ala
        275                 280                 285 att tgc att ggg gcc att gga gcc tcc aca gac tgg aac caa act gca      912
Ile Cys Ile Gly Ala Ile Gly Ala Ser Thr Asp Trp Asn Gln Thr Ala
        290                 295                 300 tat ggg ttt cca gat ccc aag acc aag gag gaa gca gac atg att ctc      960
Tyr Gly Phe Pro Asp Pro Lys Thr Lys Glu Glu Ala Asp Met Ile Leu
305                 310                 315                 320 ccg att gtt cta cag tac ctc tgc cct gtg tac att tcc ttc ttt ggg     1008
Pro Ile Val Leu Gln Tyr Leu Cys Pro Val Tyr Ile Ser Phe Phe Gly
                325                 330                 335 ctt ggt gct gtt tct gct gct gtc atg tcg tcg gct gac tca tcc atc     1056
Leu Gly Ala Val Ser Ala Ala Val Met Ser Ser Ala Asp Ser Ser Ile
                340                 345                 350 cta tca gca agt tcc atg ttt gct cgg aat atc tac cag ctt tcc ttc     1104
Leu Ser Ala Ser Ser Met Phe Ala Arg Asn Ile Tyr Gln Leu Ser Phe
            355                 360                 365 aga caa aat gca tca gac aag gaa att gtg tgg gtc atg agg atc act     1152
Arg Gln Asn Ala Ser Asp Lys Glu Ile Val Trp Val Met Arg Ile Thr
        370                 375                 380 gtg ttt gtg ttt gga gca tct gca aca gcc atg gcc ttg ctc acg aag     1200
Val Phe Val Phe Gly Ala Ser Ala Thr Ala Met Ala Leu Leu Thr Lys
385                 390                 395                 400 act gtg tat ggg ctc tgg tac ctg agc tct gac ctt gtc tac atc atc     1248
Thr Val Tyr Gly Leu Trp Tyr Leu Ser Ser Asp Leu Val Tyr Ile Ile
                405                 410                 415 atc ttc cca cag ctg ctc tgt gta ctc ttc atc aaa gga acc aac act     1296
Ile Phe Pro Gln Leu Leu Cys Val Leu Phe Ile Lys Gly Thr Asn Thr
                420                 425                 430 tat ggg gca gtt gct ggt tat att ttt gga ctt ttc ctg aga att acc     1344
Tyr Gly Ala Val Ala Gly Tyr Ile Phe Gly Leu Phe Leu Arg Ile Thr
            435                 440                 445 gga gga gag cca tat cta tac ttg cag ccc tta atc ttc tac cct ggt     1392
Gly Gly Glu Pro Tyr Leu Tyr Leu Gln Pro Leu Ile Phe Tyr Pro Gly
        450                 455                 460 tat tac cct gac aag aat ggt ata tac aat cag agg ttc cca ttt aaa     1440
Tyr Tyr Pro Asp Lys Asn Gly Ile Tyr Asn Gln Arg Phe Pro Phe Lys
465                 470                 475                 480 act ctc tcc atg gtt acc tca ttc ttt acc aac att tgt gtt tcc tat     1488
Thr Leu Ser Met Val Thr Ser Phe Phe Thr Asn Ile Cys Val Ser Tyr
                485                 490                 495 cta gcc aag tat cta ttt gaa agt gga acc ttg cct cca aaa tta gat     1536
Leu Ala Lys Tyr Leu Phe Glu Ser Gly Thr Leu Pro Pro Lys Leu Asp
                500                 505                 510 ata ttt gat gct gtt gtc tca agg cac agt gaa gag aac atg gac aag     1584
Ile Phe Asp Ala Val Val Ser Arg His Ser Glu Glu Asn Met Asp Lys
            515                 520                 525 acc att cta gtc aga aat gaa aac atc aaa tta aat gaa ctt gca cct     1632
Thr Ile Leu Val Arg Asn Glu Asn Ile Lys Leu Asn Glu Leu Ala Pro
        530                 535                 540 gta aag cct cga cag agc cta acc ctc agt tca act ttc acc aat aaa     1680
Val Lys Pro Arg Gln Ser Leu Thr Leu Ser Ser Thr Phe Thr Asn Lys
545                 550                 555                 560 gag gct ctc ctt gat gtt gat tcc agt cca gag gga tct ggg act gaa     1728
Glu Ala Leu Leu Asp Val Asp Ser Ser Pro Glu Gly Ser Gly Thr Glu
                565                 570                 575
```

```
gat aac tta caa tga                                          1743
Asp Asn Leu Gln
        580

<210> SEQ ID NO 4
<211> LENGTH: 580
<212> TYPE: PRT
<213> ORGANISM: Rattus norvegicus

<400> SEQUENCE: 4

Met Pro Phe His Val Glu Gly Leu Val Ala Ile Ile Leu Phe Tyr Leu
 1               5                  10                  15

Leu Ile Phe Leu Val Gly Ile Trp Ala Ala Trp Lys Thr Lys Asn Ser
            20                  25                  30

Gly Asn Ala Glu Glu Arg Ser Glu Ala Ile Ile Val Gly Gly Arg Asp
        35                  40                  45

Ile Gly Leu Leu Val Gly Gly Phe Thr Met Thr Ala Thr Trp Val Gly
    50                  55                  60

Gly Gly Tyr Ile Asn Gly Thr Ala Glu Ala Val Tyr Gly Pro Gly Cys
65                  70                  75                  80

Gly Leu Ala Trp Ala Gln Ala Pro Ile Gly Tyr Ser Leu Ser Leu Ile
                85                  90                  95

Leu Gly Gly Leu Phe Phe Ala Lys Pro Met Arg Ser Lys Gly Tyr Val
            100                 105                 110

Thr Met Leu Asp Pro Phe Gln Gln Ile Tyr Gly Lys Arg Met Gly Gly
        115                 120                 125

Leu Leu Phe Ile Pro Ala Leu Met Gly Glu Met Phe Trp Ala Ala Ala
    130                 135                 140

Ile Phe Ser Ala Leu Gly Ala Thr Ile Ser Val Ile Ile Asp Val Asp
145                 150                 155                 160

Val Asn Ile Ser Val Ile Val Ser Ala Leu Ile Ala Ile Leu Tyr Thr
                165                 170                 175

Leu Val Gly Gly Leu Tyr Ser Val Ala Tyr Thr Asp Val Val Gln Leu
            180                 185                 190

Phe Cys Ile Phe Ile Gly Leu Trp Ile Ser Val Pro Phe Ala Leu Ser
        195                 200                 205

His Pro Ala Val Thr Asp Ile Gly Phe Thr Ala Val His Ala Lys Tyr
    210                 215                 220

Gln Ser Pro Trp Leu Gly Thr Ile Glu Ser Val Glu Val Tyr Thr Trp
225                 230                 235                 240

Leu Asp Asn Phe Leu Leu Leu Met Leu Gly Gly Ile Pro Trp Gln Ala
                245                 250                 255

Tyr Phe Gln Arg Val Leu Ser Ser Ser Ala Thr Tyr Ala Gln Val
            260                 265                 270

Leu Ser Phe Leu Ala Ala Phe Gly Cys Leu Val Met Ala Leu Pro Ala
        275                 280                 285

Ile Cys Ile Gly Ala Ile Gly Ala Ser Thr Asp Trp Asn Gln Thr Ala
    290                 295                 300

Tyr Gly Phe Pro Asp Pro Lys Thr Lys Glu Glu Ala Asp Met Ile Leu
305                 310                 315                 320

Pro Ile Val Leu Gln Tyr Leu Cys Pro Val Tyr Ile Ser Phe Phe Gly
                325                 330                 335

Leu Gly Ala Val Ser Ala Ala Val Met Ser Ser Ala Asp Ser Ser Ile
            340                 345                 350
```

Leu Ser Ala Ser Ser Met Phe Ala Arg Asn Ile Tyr Gln Leu Ser Phe
            355                 360                 365

Arg Gln Asn Ala Ser Asp Lys Glu Ile Val Trp Val Met Arg Ile Thr
        370                 375                 380

Val Phe Val Phe Gly Ala Ser Ala Thr Met Ala Leu Leu Thr Lys
385                 390                 395                 400

Thr Val Tyr Gly Leu Trp Tyr Leu Ser Ser Asp Leu Val Tyr Ile Ile
            405                 410                 415

Ile Phe Pro Gln Leu Leu Cys Val Leu Phe Ile Lys Gly Thr Asn Thr
        420                 425                 430

Tyr Gly Ala Val Ala Gly Tyr Ile Phe Gly Leu Phe Leu Arg Ile Thr
        435                 440                 445

Gly Gly Glu Pro Tyr Leu Tyr Leu Gln Pro Leu Ile Phe Tyr Pro Gly
        450                 455                 460

Tyr Tyr Pro Asp Lys Asn Gly Ile Tyr Asn Gln Arg Phe Pro Phe Lys
465                 470                 475                 480

Thr Leu Ser Met Val Thr Ser Phe Phe Thr Asn Ile Cys Val Ser Tyr
            485                 490                 495

Leu Ala Lys Tyr Leu Phe Glu Ser Gly Thr Leu Pro Pro Lys Leu Asp
            500                 505                 510

Ile Phe Asp Ala Val Val Ser Arg His Ser Glu Glu Asn Met Asp Lys
        515                 520                 525

Thr Ile Leu Val Arg Asn Glu Asn Ile Lys Leu Asn Glu Leu Ala Pro
        530                 535                 540

Val Lys Pro Arg Gln Ser Leu Thr Leu Ser Ser Thr Phe Thr Asn Lys
545                 550                 555                 560

Glu Ala Leu Leu Asp Val Asp Ser Ser Pro Glu Gly Ser Gly Thr Glu
            565                 570                 575

Asp Asn Leu Gln
            580

<210> SEQ ID NO 5
<211> LENGTH: 1743
<212> TYPE: DNA
<213> ORGANISM: Homo sapiens
<220> FEATURE:
<221> NAME/KEY: CDS
<222> LOCATION: (1)..(1743)

<400> SEQUENCE: 5 atg gct ttc cat gtg gaa gga ctg ata gct atc atc gtg ttc tac ctt     48
Met Ala Phe His Val Glu Gly Leu Ile Ala Ile Ile Val Phe Tyr Leu
  1               5                  10                  15 cta att ttg ctg gtt gga ata tgg gct gcc tgg aga acc aaa aac agt     96
Leu Ile Leu Leu Val Gly Ile Trp Ala Ala Trp Arg Thr Lys Asn Ser
             20                  25                  30 ggc agc gca gaa gag cgc agc gaa gcc atc ata gtt ggt ggc cga gat    144
Gly Ser Ala Glu Glu Arg Ser Glu Ala Ile Ile Val Gly Gly Arg Asp
         35                  40                  45 att ggt tta ttg gtt ggt gga ttt acc atg aca gct acc tgg gtc gga    192
Ile Gly Leu Leu Val Gly Gly Phe Thr Met Thr Ala Thr Trp Val Gly
     50                  55                  60 gga ggg tat atc aat ggc aca gct gaa gca gtt tat gta cca ggt tat    240
Gly Gly Tyr Ile Asn Gly Thr Ala Glu Ala Val Tyr Val Pro Gly Tyr
 65                  70                  75                  80 ggc cta gct tgg gct cag gca cca att gga tat tct ctt agt ctg att    288
Gly Leu Ala Trp Ala Gln Ala Pro Ile Gly Tyr Ser Leu Ser Leu Ile
                 85                  90                  95

```
tta ggt ggc ctg ttc ttt gca aaa cct atg cgt tca aag ggg tat gtg      336
Leu Gly Gly Leu Phe Phe Ala Lys Pro Met Arg Ser Lys Gly Tyr Val
            100                 105                 110 acc atg tta gac ccg ttt cag caa atc tat gga aaa cgc atg ggc gga      384
Thr Met Leu Asp Pro Phe Gln Gln Ile Tyr Gly Lys Arg Met Gly Gly
            115                 120                 125 ctc ctg ttt att cct gca ctg atg gga gaa atg ttc tgg gct gca gca      432
Leu Leu Phe Ile Pro Ala Leu Met Gly Glu Met Phe Trp Ala Ala Ala
    130                 135                 140 att ttc tct gct ttg gga gcc acc atc agc gtg atc atc gat gtg gat      480
Ile Phe Ser Ala Leu Gly Ala Thr Ile Ser Val Ile Ile Asp Val Asp
145                 150                 155                 160 atg cac att tct gtc atc atc tct gca ctc att gcc act ctg tac aca      528
Met His Ile Ser Val Ile Ile Ser Ala Leu Ile Ala Thr Leu Tyr Thr
                165                 170                 175 ctg gtg gga ggg ctc tat tct gtg gcc tac act gat gtc gtt cag ctc      576
Leu Val Gly Gly Leu Tyr Ser Val Ala Tyr Thr Asp Val Val Gln Leu
            180                 185                 190 ttt tgc att ttt gta ggg ctg tgg atc agc gtc ccc ttt gca ttg tca      624
Phe Cys Ile Phe Val Gly Leu Trp Ile Ser Val Pro Phe Ala Leu Ser
        195                 200                 205 cat cct gca gtc gca gac atc ggg ttc act gct gtg cat gcc aaa tac      672
His Pro Ala Val Ala Asp Ile Gly Phe Thr Ala Val His Ala Lys Tyr
    210                 215                 220 caa aag ccg tgg ctg gga act gtt gac tca tct gaa gtc tac tct tgg      720
Gln Lys Pro Trp Leu Gly Thr Val Asp Ser Ser Glu Val Tyr Ser Trp
225                 230                 235                 240 ctt gat agt ttt ctg ttg ttg atg ctg ggt gga atc cca tgg caa gca      768
Leu Asp Ser Phe Leu Leu Leu Met Leu Gly Gly Ile Pro Trp Gln Ala
                245                 250                 255 tac ttt cag agg gtt ctc tct tct tcc tca gcc acc tat gct caa gtg      816
Tyr Phe Gln Arg Val Leu Ser Ser Ser Ser Ala Thr Tyr Ala Gln Val
            260                 265                 270 ctg tcc ttc ctg gca gct ttc ggg tgc ctg gtg atg gcc atc cca gcc      864
Leu Ser Phe Leu Ala Ala Phe Gly Cys Leu Val Met Ala Ile Pro Ala
        275                 280                 285 ata ctc att ggg gcc att gga gca tca aca gac tgg aac cag act gca      912
Ile Leu Ile Gly Ala Ile Gly Ala Ser Thr Asp Trp Asn Gln Thr Ala
    290                 295                 300 tat ggg ctt cca gat ccc aag act aca gaa gag gca gac atg att tta      960
Tyr Gly Leu Pro Asp Pro Lys Thr Thr Glu Glu Ala Asp Met Ile Leu
305                 310                 315                 320 cca att gtt ctg cag tat ctc tgc cct gtg tat att tct ttc ttt ggt     1008
Pro Ile Val Leu Gln Tyr Leu Cys Pro Val Tyr Ile Ser Phe Phe Gly
                325                 330                 335 ctt ggt gca gtt tct gct gct gtt atg tca tca gca gat tct tcc atc     1056
Leu Gly Ala Val Ser Ala Ala Val Met Ser Ser Ala Asp Ser Ser Ile
            340                 345                 350 ttg tca gca agt tcc atg ttt gca cgg aac atc tac cag ctt tcc ttc     1104
Leu Ser Ala Ser Ser Met Phe Ala Arg Asn Ile Tyr Gln Leu Ser Phe
        355                 360                 365 aga caa aat gct tcg gac aaa gaa atc gtt tgg gtt atg cga atc aca     1152
Arg Gln Asn Ala Ser Asp Lys Glu Ile Val Trp Val Met Arg Ile Thr
    370                 375                 380 gtg ttt gtg ttt gga gca tct gca aca gcc atg gcc ttg ctg acg aaa     1200
Val Phe Val Phe Gly Ala Ser Ala Thr Ala Met Ala Leu Leu Thr Lys
385                 390                 395                 400 act gtg tat ggg ctc tgg tac ctc agt tct gac ctt gtt tac atc gtt     1248
Thr Val Tyr Gly Leu Trp Tyr Leu Ser Ser Asp Leu Val Tyr Ile Val
```

```
                405                 410                 415
atc ttc ccc cag ctg ctt tgt gta ctc ttt gtt aag gga acc aac acc    1296
Ile Phe Pro Gln Leu Leu Cys Val Leu Phe Val Lys Gly Thr Asn Thr
                420                 425                 430 tat ggg gcc gtg gca ggt tat gtt tct ggc ctc ttc ctg aga ata act    1344
Tyr Gly Ala Val Ala Gly Tyr Val Ser Gly Leu Phe Leu Arg Ile Thr
                435                 440                 445 gga ggg gag cca tat ctg tat ctt cag ccc ttg atc ttc tac cct ggc    1392
Gly Gly Glu Pro Tyr Leu Tyr Leu Gln Pro Leu Ile Phe Tyr Pro Gly
                450                 455                 460 tat tac cct gat gat aat ggt ata tat aat cag aaa ttt cca ttt aaa    1440
Tyr Tyr Pro Asp Asp Asn Gly Ile Tyr Asn Gln Lys Phe Pro Phe Lys
465                 470                 475                 480 aca ctt gcc atg gtt aca tca ttc tta acc aac att tgc atc tcc tat    1488
Thr Leu Ala Met Val Thr Ser Phe Leu Thr Asn Ile Cys Ile Ser Tyr
                485                 490                 495 cta gcc aag tat cta ttt gaa agt gga acc ttg cca cct aaa tta gat    1536
Leu Ala Lys Tyr Leu Phe Glu Ser Gly Thr Leu Pro Pro Lys Leu Asp
                500                 505                 510 gta ttt gat gct gtt gtt gca aga cac agt gaa gaa aac atg gat aag    1584
Val Phe Asp Ala Val Val Ala Arg His Ser Glu Glu Asn Met Asp Lys
                515                 520                 525 aca att ctt gtc aaa aat gaa aat att aaa tta gat gaa ctt gca ctt    1632
Thr Ile Leu Val Lys Asn Glu Asn Ile Lys Leu Asp Glu Leu Ala Leu
                530                 535                 540 gtg aag cca cga cag agc atg acc ctc agc tca act ttc acc aat aaa    1680
Val Lys Pro Arg Gln Ser Met Thr Leu Ser Ser Thr Phe Thr Asn Lys
545                 550                 555                 560 gag gcc ttc ctt gat gtt gat tcc agt cca gaa ggg tct ggg act gaa    1728
Glu Ala Phe Leu Asp Val Asp Ser Ser Pro Glu Gly Ser Gly Thr Glu
                565                 570                 575 gat aat tta cag tga                                                 1743
Asp Asn Leu Gln
                580

<210> SEQ ID NO 6
<211> LENGTH: 580
<212> TYPE: PRT
<213> ORGANISM: Homo sapiens

<400> SEQUENCE: 6

Met Ala Phe His Val Glu Gly Leu Ile Ala Ile Ile Val Phe Tyr Leu
  1               5                  10                  15

Leu Ile Leu Leu Val Gly Ile Trp Ala Ala Trp Arg Thr Lys Asn Ser
                 20                  25                  30

Gly Ser Ala Glu Glu Arg Ser Glu Ala Ile Ile Val Gly Gly Arg Asp
             35                  40                  45

Ile Gly Leu Leu Val Gly Gly Phe Thr Met Thr Ala Thr Trp Val Gly
         50                  55                  60

Gly Gly Tyr Ile Asn Gly Thr Ala Glu Ala Val Tyr Val Pro Gly Tyr
 65                  70                  75                  80

Gly Leu Ala Trp Ala Gln Ala Pro Ile Gly Tyr Ser Leu Ser Leu Ile
                 85                  90                  95

Leu Gly Gly Leu Phe Phe Ala Lys Pro Met Arg Ser Lys Gly Tyr Val
                100                 105                 110

Thr Met Leu Asp Pro Phe Gln Gln Ile Tyr Gly Lys Arg Met Gly Gly
            115                 120                 125

Leu Leu Phe Ile Pro Ala Leu Met Gly Glu Met Phe Trp Ala Ala Ala
```

-continued

```
            130                 135                 140
Ile Phe Ser Ala Leu Gly Ala Thr Ile Ser Val Ile Ile Asp Val Asp
145                 150                 155                 160
Met His Ile Ser Val Ile Ile Ser Ala Leu Ile Ala Thr Leu Tyr Thr
                    165                 170                 175
Leu Val Gly Gly Leu Tyr Ser Val Ala Tyr Thr Asp Val Val Gln Leu
                180                 185                 190
Phe Cys Ile Phe Val Gly Leu Trp Ile Ser Val Pro Phe Ala Leu Ser
            195                 200                 205
His Pro Ala Val Ala Asp Ile Gly Phe Thr Ala Val His Ala Lys Tyr
210                 215                 220
Gln Lys Pro Trp Leu Gly Thr Val Asp Ser Ser Glu Val Tyr Ser Trp
225                 230                 235                 240
Leu Asp Ser Phe Leu Leu Leu Met Leu Gly Gly Ile Pro Trp Gln Ala
                245                 250                 255
Tyr Phe Gln Arg Val Leu Ser Ser Ser Ala Thr Tyr Ala Gln Val
                260                 265                 270
Leu Ser Phe Leu Ala Ala Phe Gly Cys Leu Val Met Ala Ile Pro Ala
            275                 280                 285
Ile Leu Ile Gly Ala Ile Gly Ala Ser Thr Asp Trp Asn Gln Thr Ala
290                 295                 300
Tyr Gly Leu Pro Asp Pro Lys Thr Thr Glu Glu Ala Asp Met Ile Leu
305                 310                 315                 320
Pro Ile Val Leu Gln Tyr Leu Cys Pro Val Tyr Ile Ser Phe Phe Gly
                325                 330                 335
Leu Gly Ala Val Ser Ala Ala Val Met Ser Ser Ala Asp Ser Ser Ile
            340                 345                 350
Leu Ser Ala Ser Ser Met Phe Ala Arg Asn Ile Tyr Gln Leu Ser Phe
            355                 360                 365
Arg Gln Asn Ala Ser Asp Lys Glu Ile Val Trp Val Met Arg Ile Thr
370                 375                 380
Val Phe Val Phe Gly Ala Ser Ala Thr Ala Met Ala Leu Leu Thr Lys
385                 390                 395                 400
Thr Val Tyr Gly Leu Trp Tyr Leu Ser Ser Asp Leu Val Tyr Ile Val
                405                 410                 415
Ile Phe Pro Gln Leu Leu Cys Val Leu Phe Val Lys Gly Thr Asn Thr
                420                 425                 430
Tyr Gly Ala Val Ala Gly Tyr Val Ser Gly Leu Phe Leu Arg Ile Thr
            435                 440                 445
Gly Gly Glu Pro Tyr Leu Tyr Leu Gln Pro Leu Ile Phe Tyr Pro Gly
450                 455                 460
Tyr Tyr Pro Asp Asp Asn Gly Ile Tyr Asn Gln Lys Phe Pro Phe Lys
465                 470                 475                 480
Thr Leu Ala Met Val Thr Ser Phe Leu Thr Asn Ile Cys Ile Ser Tyr
                485                 490                 495
Leu Ala Lys Tyr Leu Phe Glu Ser Gly Thr Leu Pro Pro Lys Leu Asp
                500                 505                 510
Val Phe Asp Ala Val Val Ala Arg His Ser Glu Glu Asn Met Asp Lys
            515                 520                 525
Thr Ile Leu Val Lys Asn Glu Asn Ile Lys Leu Asp Glu Leu Ala Leu
            530                 535                 540
Val Lys Pro Arg Gln Ser Met Thr Leu Ser Ser Thr Phe Thr Asn Lys
545                 550                 555                 560
```

```
Glu Ala Phe Leu Asp Val Asp Ser Ser Pro Glu Gly Ser Gly Thr Glu
                565                 570                 575

Asp Asn Leu Gln
            580

<210> SEQ ID NO 7
<211> LENGTH: 1743
<212> TYPE: DNA
<213> ORGANISM: Mus musculus
<220> FEATURE:
<221> NAME/KEY: CDS
<222> LOCATION: (1)..(1743)

<400> SEQUENCE: 7 atg tct ttc cac gta gaa gga ctg gta gct att atc ctc ttc tac ctc      48
Met Ser Phe His Val Glu Gly Leu Val Ala Ile Ile Leu Phe Tyr Leu
  1               5                  10                  15 ctt ata ttt ctg gtt gga ata tgg gct gca tgg aaa acc aaa aac agc      96
Leu Ile Phe Leu Val Gly Ile Trp Ala Ala Trp Lys Thr Lys Asn Ser
             20                  25                  30 ggc aac cca gaa gag cac agt gaa gcc atc ata gtc ggg ggc cgt gac     144
Gly Asn Pro Glu Glu His Ser Glu Ala Ile Ile Val Gly Gly Arg Asp
         35                  40                  45 att ggt ttg ttg gtt ggt ggt ttt acc atg aca gcc acc tgg gtt gga     192
Ile Gly Leu Leu Val Gly Gly Phe Thr Met Thr Ala Thr Trp Val Gly
     50                  55                  60 gga ggc tac atc aat ggg aca gca gaa gca gtg tat ggg cca ggt tgt     240
Gly Gly Tyr Ile Asn Gly Thr Ala Glu Ala Val Tyr Gly Pro Gly Cys
 65                  70                  75                  80 ggt cta gct tgg gct cag gca ccc att gga tat tct ctg agt cta att     288
Gly Leu Ala Trp Ala Gln Ala Pro Ile Gly Tyr Ser Leu Ser Leu Ile
                 85                  90                  95 tta ggt ggt ctg ttt ttt gcg aaa cct atg cgt tcc aag gga tat gtg     336
Leu Gly Gly Leu Phe Phe Ala Lys Pro Met Arg Ser Lys Gly Tyr Val
            100                 105                 110 act atg tta gac cca ttt caa cag atc tat gga aag cgc atg ggt ggg     384
Thr Met Leu Asp Pro Phe Gln Gln Ile Tyr Gly Lys Arg Met Gly Gly
        115                 120                 125 ctg ctc ttc atc cct gca ctg atg gga gag atg ttc tgg gct gca gca     432
Leu Leu Phe Ile Pro Ala Leu Met Gly Glu Met Phe Trp Ala Ala Ala
    130                 135                 140 att ttc tct gca tta ggg gcc acc atc agc gtg atc att gat gtg gat     480
Ile Phe Ser Ala Leu Gly Ala Thr Ile Ser Val Ile Ile Asp Val Asp
145                 150                 155                 160 gtg aac ata tcg gtc att gtc tct gca ctc att gcc att ctt tat acc     528
Val Asn Ile Ser Val Ile Val Ser Ala Leu Ile Ala Ile Leu Tyr Thr
                165                 170                 175 cta gtg ggt ggg ctc tac tct gtg gca tat act gat gtt gtc cag cta     576
Leu Val Gly Gly Leu Tyr Ser Val Ala Tyr Thr Asp Val Val Gln Leu
            180                 185                 190 ttc tgc att ttt ata gga ctg tgg atc agt gtc cct ttt gcc ctg tca     624
Phe Cys Ile Phe Ile Gly Leu Trp Ile Ser Val Pro Phe Ala Leu Ser
        195                 200                 205 cat cct gca gtc acc gac atc gga ttc aca gct gtg cat gct aaa tac     672
His Pro Ala Val Thr Asp Ile Gly Phe Thr Ala Val His Ala Lys Tyr
    210                 215                 220 cag agt ccc tgg ctg gga acc att gaa tca gtt gaa gtc tac acc tgg     720
Gln Ser Pro Trp Leu Gly Thr Ile Glu Ser Val Glu Val Tyr Thr Trp
225                 230                 235                 240 ctt gat aat ttt ctg tta ttg atg ctg ggt gga atc cca tgg caa gcc     768
```

-continued

```
            Leu Asp Asn Phe Leu Leu Leu Met Leu Gly Gly Ile Pro Trp Gln Ala
                            245                 250                 255 tac ttc cag agg gtc ctc tct tca tcc tca gcc acc tat gct cag gta         816
Tyr Phe Gln Arg Val Leu Ser Ser Ser Ser Ala Thr Tyr Ala Gln Val
                260                 265                 270 ctg tcc ttc ctg gca gct ttt ggg tgc ctg gtg atg gct cta ccc gcc         864
Leu Ser Phe Leu Ala Ala Phe Gly Cys Leu Val Met Ala Leu Pro Ala
            275                 280                 285 ata tgc ata gga gct att gga gct tcc aca gac tgg aac cag act gcc         912
Ile Cys Ile Gly Ala Ile Gly Ala Ser Thr Asp Trp Asn Gln Thr Ala
        290                 295                 300 tac ggg tat cca gat ccc aag act aag gag gaa gca gac atg att ctc         960
Tyr Gly Tyr Pro Asp Pro Lys Thr Lys Glu Glu Ala Asp Met Ile Leu
305                 310                 315                 320 ccg atc gtt ctg cag tac ctc tgc cct gtg tac atc tcc ttc ttt ggg        1008
Pro Ile Val Leu Gln Tyr Leu Cys Pro Val Tyr Ile Ser Phe Phe Gly
                325                 330                 335 ctt ggt gct gtt tca gct gct gtc atg tcc tca gct gac tcg tcc atc        1056
Leu Gly Ala Val Ser Ala Ala Val Met Ser Ser Ala Asp Ser Ser Ile
                340                 345                 350 ctg tcg gcg agt tct atg ttt gct cgg aat atc tac cag ctt tcc ttc        1104
Leu Ser Ala Ser Ser Met Phe Ala Arg Asn Ile Tyr Gln Leu Ser Phe
            355                 360                 365 aga caa aat gca tca gac aag gaa att gtg tgg gtc atg agg atc act        1152
Arg Gln Asn Ala Ser Asp Lys Glu Ile Val Trp Val Met Arg Ile Thr
370                 375                 380 gtg ctt gtg ttc gga gca tct gca aca gcc atg gct ttg ctg acg aag        1200
Val Leu Val Phe Gly Ala Ser Ala Thr Ala Met Ala Leu Leu Thr Lys
385                 390                 395                 400 act gtg tat ggg ctc tgg tac ctg agc tct gac ctt gtc tac atc atc        1248
Thr Val Tyr Gly Leu Trp Tyr Leu Ser Ser Asp Leu Val Tyr Ile Ile
                405                 410                 415 atc ttc cca cag ctg ctc tgt gta ctc ttc atc aaa gga acc aac act        1296
Ile Phe Pro Gln Leu Leu Cys Val Leu Phe Ile Lys Gly Thr Asn Thr
                420                 425                 430 tat ggg gca gtt gct ggt tat att ttt gga cta ttc ctg aga att act        1344
Tyr Gly Ala Val Ala Gly Tyr Ile Phe Gly Leu Phe Leu Arg Ile Thr
            435                 440                 445 gga gga gag cca tat cta tac ttg cag ccc tta atc ttc tac cct ggt        1392
Gly Gly Glu Pro Tyr Leu Tyr Leu Gln Pro Leu Ile Phe Tyr Pro Gly
        450                 455                 460 tat tac tct gac aag aat ggt ata tac aat cag agg ttc cca ttt aaa        1440
Tyr Tyr Ser Asp Lys Asn Gly Ile Tyr Asn Gln Arg Phe Pro Phe Lys
465                 470                 475                 480 act ctc tcc atg gtt acc tca ttc ttt acc aac att tgt gtt tct tat        1488
Thr Leu Ser Met Val Thr Ser Phe Phe Thr Asn Ile Cys Val Ser Tyr
                485                 490                 495 cta gcc aag tat cta ttt gaa agt gga acc ttg cct cca aaa tta gat        1536
Leu Ala Lys Tyr Leu Phe Glu Ser Gly Thr Leu Pro Pro Lys Leu Asp
                500                 505                 510 gta ttt gat gct gtt gtc gca agg cac agt gaa gag aac atg gac aag        1584
Val Phe Asp Ala Val Val Ala Arg His Ser Glu Glu Asn Met Asp Lys
            515                 520                 525 acc att cta gtc aga aat gaa aat atc aaa tta aat gaa ctt gca cct        1632
Thr Ile Leu Val Arg Asn Glu Asn Ile Lys Leu Asn Glu Leu Ala Pro
        530                 535                 540 gtg aaa cct cgg cag agc cta acc ctc agt tca act ttc acc aat aag        1680
Val Lys Pro Arg Gln Ser Leu Thr Leu Ser Ser Thr Phe Thr Asn Lys
545                 550                 555                 560
```

-continued

```
gag gcc ctc ctt gat gtt gat tcc agt ccg gag ggg tct ggg act gaa    1728
Glu Ala Leu Leu Asp Val Asp Ser Ser Pro Glu Gly Ser Gly Thr Glu
                565                 570                 575 gat aac tta caa tga                                                1743
Asp Asn Leu Gln
        580
```

<210> SEQ ID NO 8
<211> LENGTH: 580
<212> TYPE: PRT
<213> ORGANISM: Mus musculus

<400> SEQUENCE: 8

```
Met Ser Phe His Val Glu Gly Leu Val Ala Ile Ile Leu Phe Tyr Leu
  1               5                  10                  15

Leu Ile Phe Leu Val Gly Ile Trp Ala Ala Trp Lys Thr Lys Asn Ser
             20                  25                  30

Gly Asn Pro Glu Glu His Ser Glu Ala Ile Ile Val Gly Gly Arg Asp
         35                  40                  45

Ile Gly Leu Leu Val Gly Gly Phe Thr Met Thr Ala Thr Trp Val Gly
     50                  55                  60

Gly Gly Tyr Ile Asn Gly Thr Ala Glu Ala Val Tyr Gly Pro Gly Cys
 65                  70                  75                  80

Gly Leu Ala Trp Ala Gln Ala Pro Ile Gly Tyr Ser Leu Ser Leu Ile
                 85                  90                  95

Leu Gly Gly Leu Phe Phe Ala Lys Pro Met Arg Ser Lys Gly Tyr Val
            100                 105                 110

Thr Met Leu Asp Pro Phe Gln Gln Ile Tyr Gly Lys Arg Met Gly Gly
        115                 120                 125

Leu Leu Phe Ile Pro Ala Leu Met Gly Glu Met Phe Trp Ala Ala Ala
    130                 135                 140

Ile Phe Ser Ala Leu Gly Ala Thr Ile Ser Val Ile Ile Asp Val Asp
145                 150                 155                 160

Val Asn Ile Ser Val Ile Val Ser Ala Leu Ile Ala Ile Leu Tyr Thr
                165                 170                 175

Leu Val Gly Gly Leu Tyr Ser Val Ala Tyr Thr Asp Val Val Gln Leu
            180                 185                 190

Phe Cys Ile Phe Ile Gly Leu Trp Ile Ser Val Pro Phe Ala Leu Ser
        195                 200                 205

His Pro Ala Val Thr Asp Ile Gly Phe Thr Ala Val His Ala Lys Tyr
    210                 215                 220

Gln Ser Pro Trp Leu Gly Thr Ile Glu Ser Val Glu Val Tyr Thr Trp
225                 230                 235                 240

Leu Asp Asn Phe Leu Leu Met Leu Gly Ile Pro Trp Gln Ala
                245                 250                 255

Tyr Phe Gln Arg Val Leu Ser Ser Ser Ala Thr Tyr Ala Gln Val
            260                 265                 270

Leu Ser Phe Leu Ala Ala Phe Gly Cys Leu Val Met Ala Leu Pro Ala
        275                 280                 285

Ile Cys Ile Gly Ala Ile Gly Ala Ser Thr Asp Trp Asn Gln Thr Ala
    290                 295                 300

Tyr Gly Tyr Pro Asp Pro Lys Thr Lys Glu Ala Asp Met Ile Leu
305                 310                 315                 320

Pro Ile Val Leu Gln Tyr Leu Cys Pro Val Tyr Ile Ser Phe Phe Gly
                325                 330                 335
```

-continued

```
Leu Gly Ala Val Ser Ala Ala Val Met Ser Ser Ala Asp Ser Ser Ile
            340                 345                 350

Leu Ser Ala Ser Ser Met Phe Ala Arg Asn Ile Tyr Gln Leu Ser Phe
            355                 360                 365

Arg Gln Asn Ala Ser Asp Lys Glu Ile Val Trp Val Met Arg Ile Thr
        370                 375                 380

Val Leu Val Phe Gly Ala Ser Ala Thr Ala Met Ala Leu Leu Thr Lys
385                 390                 395                 400

Thr Val Tyr Gly Leu Trp Tyr Leu Ser Ser Asp Leu Val Tyr Ile Ile
                405                 410                 415

Ile Phe Pro Gln Leu Leu Cys Val Leu Phe Ile Lys Gly Thr Asn Thr
            420                 425                 430

Tyr Gly Ala Val Ala Gly Tyr Ile Phe Gly Leu Phe Leu Arg Ile Thr
            435                 440                 445

Gly Gly Glu Pro Tyr Leu Tyr Leu Gln Pro Leu Ile Phe Tyr Pro Gly
    450                 455                 460

Tyr Tyr Ser Asp Lys Asn Gly Ile Tyr Asn Gln Arg Phe Pro Phe Lys
465                 470                 475                 480

Thr Leu Ser Met Val Thr Ser Phe Phe Thr Asn Ile Cys Val Ser Tyr
                485                 490                 495

Leu Ala Lys Tyr Leu Phe Glu Ser Gly Thr Leu Pro Pro Lys Leu Asp
                500                 505                 510

Val Phe Asp Ala Val Val Ala Arg His Ser Glu Glu Asn Met Asp Lys
            515                 520                 525

Thr Ile Leu Val Arg Asn Glu Asn Ile Lys Leu Asn Glu Leu Ala Pro
        530                 535                 540

Val Lys Pro Arg Gln Ser Leu Thr Leu Ser Ser Thr Phe Thr Asn Lys
545                 550                 555                 560

Glu Ala Leu Leu Asp Val Asp Ser Ser Pro Glu Gly Ser Gly Thr Glu
                565                 570                 575

Asp Asn Leu Gln
            580
```